United States Patent
Herrmann et al.

(10) Patent No.: US 9,212,335 B2
(45) Date of Patent: Dec. 15, 2015

(54) EQUILIBRATED DYNAMIC MIXTURES TO CONTROL THE RELEASE OF PERFUMING ALDEHYDES AND KETONES

(75) Inventors: Andreas Herrmann, Geneva (CH); Christian Chapuis, Geneva (CH)

(73) Assignee: Firmenich SA, Geneva (CH)

( * ) Notice: Subject to any disclaimer, the term of this patent is extended or adjusted under 35 U.S.C. 154(b) by 91 days.

(21) Appl. No.: 14/111,125

(22) PCT Filed: Apr. 2, 2012

(86) PCT No.: PCT/EP2012/055926
§ 371 (c)(1),
(2), (4) Date: Oct. 10, 2013

(87) PCT Pub. No.: WO2012/139912
PCT Pub. Date: Oct. 18, 2012

(65) Prior Publication Data
US 2014/0038873 A1  Feb. 6, 2014

Related U.S. Application Data

(60) Provisional application No. 61/474,785, filed on Apr. 13, 2011.

(30) Foreign Application Priority Data

Apr. 13, 2011 (EP) .................................. 11162180

(51) Int. Cl.
*C11B 9/00* (2006.01)
*C07D 233/02* (2006.01)
(Continued)

(52) U.S. Cl.
CPC ................ *C11B 5/0064* (2013.01); *A61K 8/41* (2013.01); *A61K 8/4913* (2013.01); *A61Q 13/00* (2013.01); *C07D 233/02* (2013.01);
(Continued)

(58) Field of Classification Search
CPC ...... C11B 9/00; C07D 233/02; C07D 239/04; C11D 3/30; C11D 3/50; A61Q 13/00
See application file for complete search history.

(56) References Cited

U.S. PATENT DOCUMENTS

2005/0239667 A1  10/2005  Bettiol et al.

FOREIGN PATENT DOCUMENTS

DE  10 2005 062175 A1  6/2007
WO  WO 2000/002991 A1  1/2000
(Continued)

OTHER PUBLICATIONS

International Search Report and Written Opinion, application PCT/EP2012/052871, mailed Jul. 5, 2012.
Jurcik et al., Tetrahedron, vol. 60, n° 14, pp. 3205-3210, 2004.
Rinnova et al., Journal of Combinatorial Chemistry, ACS, vol. 4, n° 3, pp. 209-213, 2002.
International Search Report and Written Opinion, Application No. PCT/EP2012/055926, Jul. 5, 2012.
(Continued)

*Primary Examiner* — Brian P Mruk
(74) *Attorney, Agent, or Firm* — Winston & Strawn LLP

(57) ABSTRACT

The present invention concerns a dynamic mixture obtained by combining, in the presence of water, at least one diamine derivative, comprising at least one heteroaryl moiety, with at least two perfuming aldehydes and/or ketones. The invention's mixture is capable of releasing in a controlled and prolonged manner said perfuming compounds, in particular perfuming ingredients, into the surrounding environment. The invention's dynamic mixture gives rise to a more evenly distributed positive effect for the release of the different carbonyl compounds which are part of the mixture than other examples reported in the prior art.

20 Claims, 2 Drawing Sheets

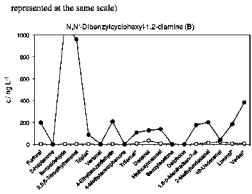

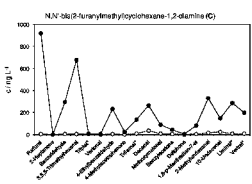

(51) Int. Cl.
  *C07D 239/04* (2006.01)
  *C11D 3/30* (2006.01)
  *C11D 3/50* (2006.01)
  *A61Q 13/00* (2006.01)
  *C11B 5/00* (2006.01)
  *C07D 471/04* (2006.01)
  *A61K 8/41* (2006.01)
  *A61K 8/49* (2006.01)

(52) U.S. Cl.
  CPC ............ *C07D 239/04* (2013.01); *C07D 471/04* (2013.01); *C11B 9/0003* (2013.01); *C11D 3/502* (2013.01); *C11D 3/507* (2013.01)

(56) References Cited

FOREIGN PATENT DOCUMENTS

| WO | WO 2008/093272 | * | 8/2008 | ........... C07D 239/04 |
| WO | WO 2008/093272 A2 | | 8/2008 | |
| WO | 2010/142480 A1 | | 12/2010 | |

OTHER PUBLICATIONS

Jaganyi et al., "A tripodal tris(thiophene) derivative of hexahydropyrimidine and its ladder-like extended structure," Acta Cryst., E63: o2388-o2390 (2007).

* cited by examiner

Figure 1 : Comparison of the headspace concentrations measured on dry fabric for a mixture of 18 volatile aldehydes and ketones in the presence (solid line) or absence (dotted line) of N,N'-dibenzylethane-1,2-diamine (B) and N,N'-bis(2-furanylmethyl)cyclohexane-1,2-diamine (C) showing the more evenly distributed increase in performance of C with respect to B (data are represented at the same scale)

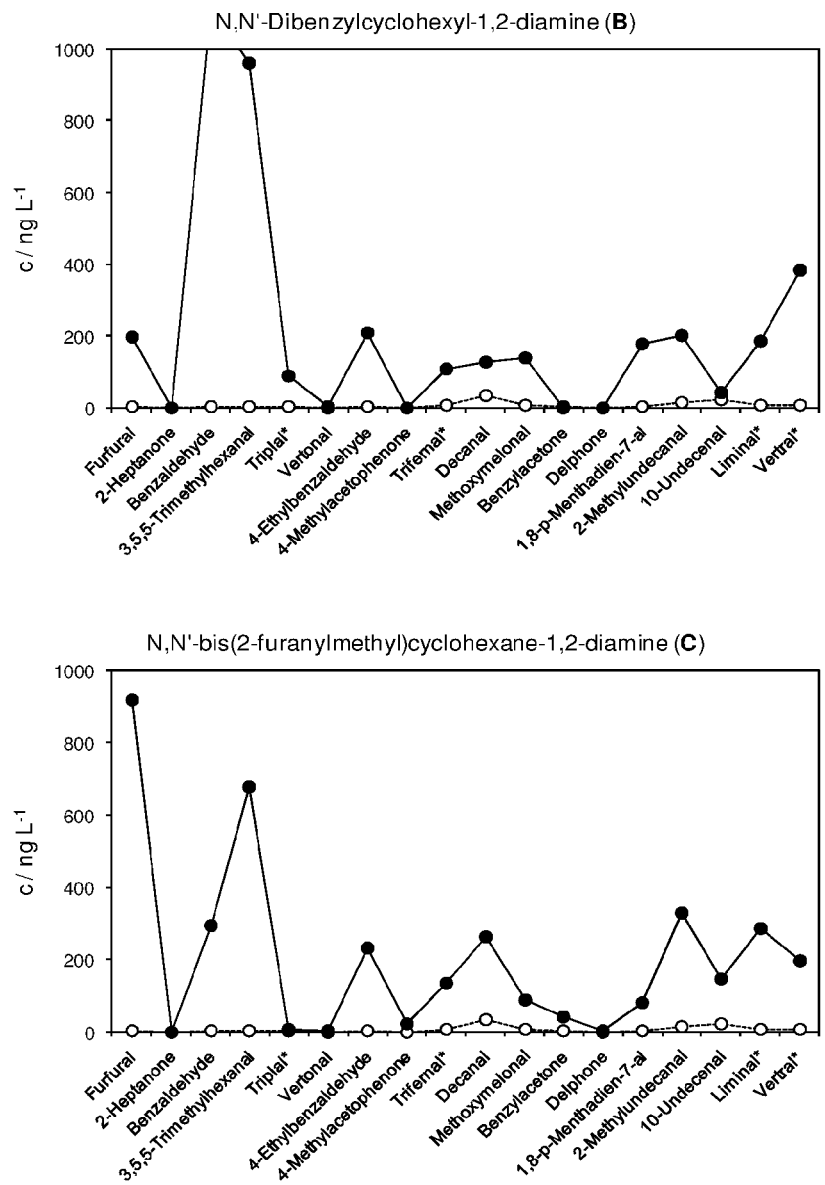

Figure 2: Comparison of the headspace concentrations measured on dry fabric for a mixture of 18 volatile aldehydes and ketones in the presence (solid line) or absence (dotted line) of N,N'-dibenzylpropane-1,3-diamine (H) and N,N'-bis(2-furanylmethyl)propane-1,3-diamine (I) showing the more evenly distributed increase in performance of I with respect to H (data are represented at the same scale)

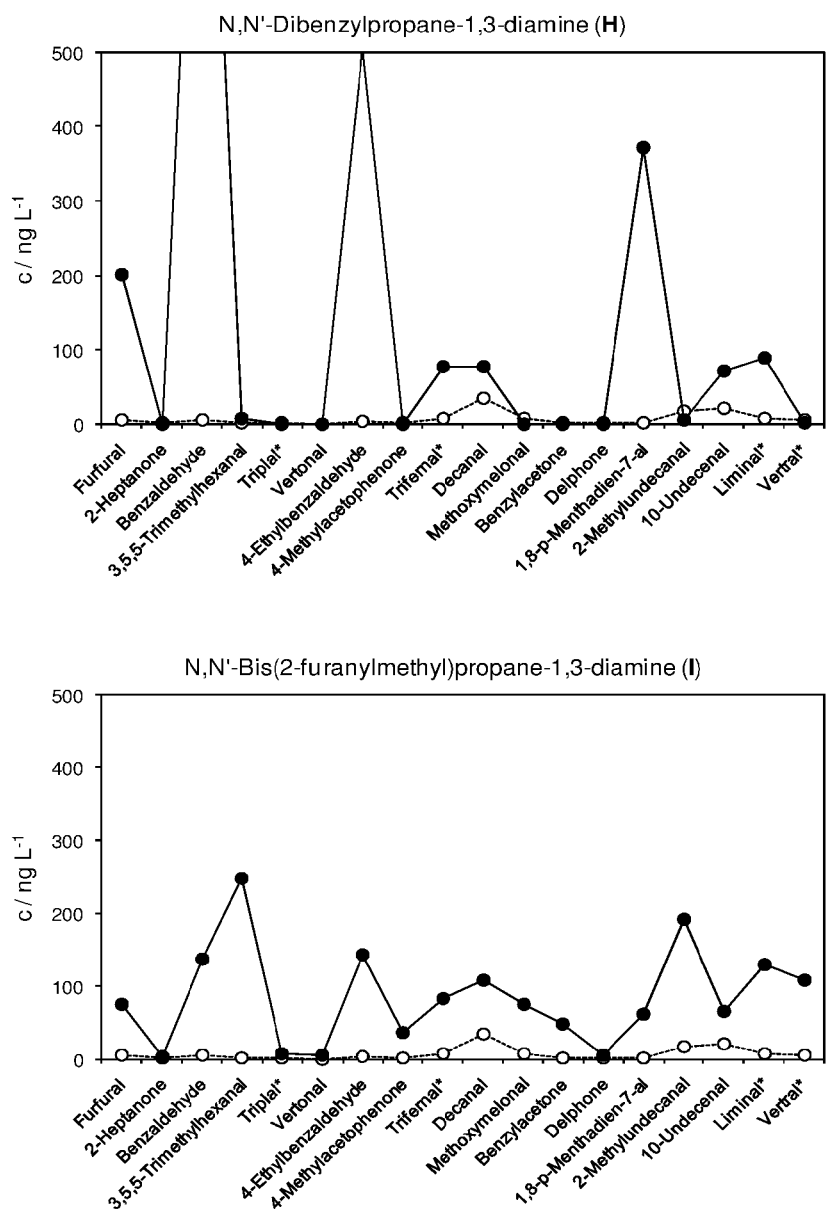

EQUILIBRATED DYNAMIC MIXTURES TO CONTROL THE RELEASE OF PERFUMING ALDEHYDES AND KETONES

CROSS REFERENCE TO RELATED APPLICATIONS

This application is a 371 of International application no. PCT/EP2012/055926 filed Apr. 2, 2012, which claims the benefit of provisional application 61/474,785 filed Apr. 13, 2011 and European application 11162180.1 also filed Apr. 13, 2011.

1. Technical Field

The present invention concerns a dynamic mixture obtained by combining, in the presence of water, at least one diamine derivative of formula (I), as defined further below, with at least two perfuming aldehydes and/or ketones. The invention's mixture is capable of releasing in a controlled and prolonged manner said perfuming compounds into the surrounding environment.

The present invention concerns also the use of said dynamic mixtures as perfuming ingredients as well as the perfuming compositions or perfumed articles comprising the invention's mixtures. A further object of the present invention is the use of said diamine derivatives as additives to prolong the perfuming effect of particular aldehydes or ketones.

2. Prior Art

The perfume industry has a particular interest for compositions or additives which are capable of prolonging or enhancing the perfuming effect of a mixture of several fragrances at the same time over a certain period of time. It is particularly desirable to obtain long-lasting properties for standard perfumery raw materials which are too volatile or have a poor substantivity by themselves, or which are only deposited in a small amount onto the surface of the final application. Furthermore, some of the perfumery ingredients, especially aldehydes, are unstable and need to be protected against slow degradation prior to their use. Long-lasting perfumes are desirable for various applications, as for example fine or functional perfumery or cosmetic preparations. The washing and softening of textiles is a particular field in which there is a constant quest to enable the effect of perfuming substances, in particular perfumes, to be effective for a certain period of time after washing, softening and drying. Indeed, many substances having odors which are particularly suitable for this type of application are known to lack tenacity on laundry, or do not remain on the laundry when rinsed, with the result that their perfuming effect is experienced only briefly and not very intensely. Given the importance of this type of application in the perfume industry, research in this field has been sustained, in particular with the aim of finding new, and more effective solutions to the aforementioned problems.

A variety of precursor compounds which release perfuming material by a chemical reaction during or after application (using $O_2$, light, enzymes, water (pH) or temperature as the release trigger) have been described as an alternative to encapsulation systems. In general, due to their inherent instability, the precursors often decompose in the application base during storage and thus release their fragrance raw material before the desired use (e.g. see WO 00/02991, US 2005/0239667).

More recently, DE 10-2005-062175 reported aminal derivatives as classical pro-perfumes, i.e. having "a better stability against hydrolysis". In this document, the principle of generating dynamic mixtures is never mentioned. The aminals reported are essentially obtained from diamines which are alkyl- or phenyl-substituted acyclic amines, which have to be prepared separately prior to their use. WO 2010/142480 describes N,N'-dimethyl diamines capable of increasing the intensity and lastingness of the odor impression of aldehydes (e.g. octanal). However, these diamines increase the intensity and lastingness of mixtures of fragrance aldehydes and ketones only marginally and thus do not represent a considerable advantage in application.

Furthermore, in WO 08/093,272 is reported a particular class of dibenzyl diamines which can be added to a perfuming composition to prolong or boost the perfuming effect of some of its ingredients. However, although the system reported in WO 08/093,272 is more efficient than the one described in DE 10-2005-062175 or in WO 2010/142480, it can be seen from the examples (e.g. see FIG. 3 of WO 08/093,272) that the dibenzyl diamine shows a prolonging or boosting effect which is not evenly distributed across the individual perfuming aldehydes and/or ketones in the mixture. This is a further problem, indeed perfumes are mixtures of different individual perfuming compounds (fragrances) and thus it is in particular desirable to simultaneously increase the long-lastingness of as much as possible fragrances and at the same time to avoid odor profile distortions over time, instead of increasing the performance of some ingredients only.

Therefore there is a need for a system capable of improving and enhancing over time the release performances of the perfuming ingredients comprising a carbonyl functional group, e.g. proving an increased headspace concentration of the perfuming ingredient in application. And furthermore, there is also a need for a system providing a more evenly distributed positive effect of the different constituents of the mixture or at least being complementary to the diamines of the prior art.

We have now found that the use of diamine derivatives different from the ones defined in the prior art (e.g. di-alkyl or cyclic and/or di-benzylic ones) as defined further below improves the performance of volatile aldehydes in practical applications by several orders of magnitude by the in situ formation of dynamic mixtures and that this improvement is more evenly distributed than, or is complementary to, the systems described in WO 08/093,272.

To the best of our knowledge, none of the compositions of the present invention have been described for the controlled and/or improved delivery of standard (i.e. of current use) perfumery aldehydes or ketones.

BRIEF DESCRIPTION OF THE DRAWINGS

FIG. 1 includes graphs (B) and (C) which show a comparison of headspace concentrations measured on dry fabric for a mixture of 18 volatile aldehydes and ketones in the presence or absence of N,N'-dibenzylcyclohexane-1,2-diamine (B) or N,N'-bis(2-furanylmethyl)cyclohexane-1,2-diamine (C); and FIG. 2 includes graphs (H) and (I) which show a comparison of headspace concentrations measured on dry fabric for a mixture of 18 volatile aldehydes and ketones in the presence or absence of N,N'-dibenzylpropane-1,3-diamine (H) or N,N'-bis(2-furanylmethyl)propane-1,3-diamine (I).

DESCRIPTION OF THE INVENTION

We have now surprisingly found that a dynamic mixture, obtainable by combining, in the presence of water, at least one diamine derivative of formula (I) (hereinafter also referred to as "invention's diamine") with at least two perfuming aldehydes and/or ketones is a valuable perfuming ingredient capable of releasing, in a controlled and prolonged manner, said perfuming aldehydes and/or ketones and, at the same time, giving a more evenly distributed effect with mixtures of aldehydes and/or ketones.

As "dynamic mixture" we mean here a composition comprising a solvent (e.g. a water-containing medium), several starting components as well as several addition products that are the results of reversible reactions between the various starting components. It is believed that said dynamic mixtures take advantage from reversible chemical reactions, in particular from the formation and dissociation by reversible condensation between the carbonyl group of the perfuming aldehyde or ketone and the two NH moieties of the diamine derivative of formula (I). The ratio between the various starting and addition products depends on the equilibrium constant of each possible reaction between the starting components. The usefulness of said "dynamic mixture" derives from a synergistic effect between all the components.

By the term "perfuming" we mean here that the aldehyde or ketone to which it is referred is capable of bringing a perfuming benefit or effect into its surrounding environment. A "perfuming aldehyde or ketone" is a compound which is of current use in the perfumery industry, i.e. a compound which is used as perfuming ingredient in perfuming preparations or compositions in order to impart a hedonic effect. In other words, such an aldehyde or ketone, to be considered as being a perfuming one, must be recognized by a person skilled in the art of perfumery as being able to impart or modify in a positive or pleasant way the odor of a composition, and not just as having an odor. For a person skilled in the art it is also evident that said perfuming aldehydes or ketones are inherently volatile compounds.

From now on we will refer to said "perfuming aldehydes and/or ketones" also as "perfuming compounds".

As previously mentioned, the invention's dynamic mixture enables a controlled release of one or several perfuming compounds. Such a behavior makes the invention's dynamic mixture particularly suitable as perfuming ingredient. Consequently, the use of an invention's dynamic mixture as perfuming ingredient is an object of the present invention. In particular it concerns a method to confer, enhance, improve or modify the odor properties of a perfuming composition or of a perfumed article, which method comprises adding to said composition or article an effective amount of an invention's dynamic mixture.

Now, the present invention concerns a use as perfuming ingredient of a dynamic mixture, for the controlled release of perfuming aldehydes and/or ketones, obtainable by reacting, in a water-containing medium, i) at least two perfuming aldehydes and/or ketones each having a molecular weight comprised between 80 and 230 g/mol, in particular being selected from the group consisting of the $C_{5-20}$ perfuming aldehydes and/or the $C_{5-20}$ perfuming ketones;

with ii) at least one derivative of formula

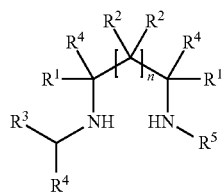

(I)

wherein:

n is 0 or 1;

each $R^1$ represents, independently of each other, a hydrogen atom, a phenyl group optionally substituted, or a $C_{1-10}$ alkyl or alkenyl group optionally substituted; if n=0, two $R^1$ taken together represent a $C_4$ group forming with the carbon atoms to which they are linked an aromatic ring which is optionally substituted;

each $R^2$ represents, independently of each other, a hydrogen atom, a phenyl group optionally substituted, or a $C_{1-10}$ alkyl or alkenyl group optionally substituted; two $R^2$ or two $R^1$ or one $R^1$ and one $R^2$, taken together, may form a $C_{3-8}$ alkanediyl or alkenediyl group;

$R^3$ represents a $C_{3-5}$ heteroaryl group optionally substituted; or $R^3$ and the adjacent $R^1$, taken together, represent with the carbon atoms to which they are linked and the NH group between them a 1H-pyrrole ring;

each $R^4$ represents, independently of each other, a hydrogen atom or a methyl group; and $R^5$ represents a $CHR^3R^4$ group, a benzyl group optionally substituted or a $C_{1-10}$ alkyl or alkenyl group; or $R^5$ and the adjacent $R^1$, taken together, represent a $C_{3-5}$ group forming with the carbon and nitrogen atom to which they are linked a saturated ring which is optionally substituted with a $CHR^3R^4$ group or a $CH_2NHCHR^3R^4$ group or one or two $C_{1-4}$ alkyl groups.

Examples of possible substituents of said $R^1$ or $R^2$ comprise one, two or three groups such as $NR^6_2$, $(NR^6R^7_2)X$, $OR^7$, $SO_3M$, $COOR^8$ or $R^6$, with $R^6$ representing a phenyl group optionally substituted by a $C_1$-$C_{10}$, or $C_1$-$C_4$, hydrocarbon group or representing a $C_1$ to $C_{10}$ alkyl or alkenyl group optionally comprising from 1 to 5 oxygen atoms, $R^7$ representing a hydrogen atom or a $R^6$ group, M representing a hydrogen atom or an alkali metal ion, $R^8$ representing a M group or a $R^6$ group and X representing a halogen atom or a sulphate.

Examples of possible substituents of said $R^3$ or $R^5$ comprise one, two or three groups selected amongst i) halogens ii) $C_{5-12}$ cycloalkyl or cycloalkenyl, iii) $C_{1-10}$ alkoxy, alkyl, alkenyl, polyalkylene glycols or halo- or perhalo-hydrocarbons, iv) $COOR^8$ wherein $R^8$ is as defined above, v) $CH_2OH$ or CHO groups, or vi) a benzyl group or a fused or non-fused phenyl or indanyl group, said groups being optionally substituted by one, two or three halogen, $C_{1-8}$ alkyl, alkoxy, amino, nitro, ester, sulfonate or halo- or perhalo-hydrocarbon groups.

The dynamic mixture is obtained by reacting one or more of the invention's diamines with one or more perfuming ingredients in a water-containing medium. By "water-containing medium" we mean here a dispersing medium comprising at least 10% w/w, or even 30% w/w, of water and optionally an aliphatic alcohol such as a $C_1$ to $C_3$ alcohol, for example ethanol. More preferably, said medium comprises at least 50% w/w, or even 70%, water optionally containing up to 30% of a surfactant. According to a particular embodiment of the invention, the water-containing medium may have a pH comprised between 2 and 11, and in particular between 3 and 10. As the diamines according to the present invention act as bases, they might increase the pH of the medium in which they are intended to be used. The pH of the medium can be re-adjusted (to be acidic) by adding an acid. The nature and type of the acid do not warrant a more detailed description here, which in any case would not be exhaustive, the skilled person being able to select them on the basis of its general knowledge and according to intended use or application. As examples for some of the preferred acids, one might cite mineral acids such as hydrochloric acid, phosphoric acid or sulfuric acid, or organic acids such as formic acid, acetic acid or citric acid.

According to a particular embodiment of the invention, the preferred derivatives of formula (I) are those wherein:

n is 0 or 1;

each $R^1$ represents, independently of each other, a hydrogen atom, a phenyl group optionally substituted, or a $C_{1-6}$ alkyl group optionally substituted;

each $R^2$ represents, independently of each other, a hydrogen atom, a phenyl group optionally substituted, or a $C_{1-6}$ alkyl group optionally substituted; two $R^2$ or two $R^1$ or one $R^1$ and one $R^2$, taken together, may form a $C_{3-6}$ alkanediyl group; or, if n=0, two $R^1$ taken together represent a $C_4$ group forming with the carbon atoms to which they are linked an aromatic ring;

$R^3$ represents a $C_{3-5}$ heteroaryl group optionally substituted; or $R^3$ and the adjacent $R^1$, taken together, represent with the carbon atoms to which they are linked and the NH group between them a 1H-pyrrole ring;

$R^4$ represents a hydrogen atom or a methyl group; and $R^5$ represents a $CHR^3R^4$ group, a benzyl group optionally substituted or a $C_{1-6}$ alkyl group; or $R^5$ and the adjacent $R^1$, taken together, represent a $C_{3-5}$ group forming with the carbon and nitrogen atom to which they are linked a saturated ring which is optionally substituted.

According to any one of the above embodiments of the invention, possible substituents of said $R^1$ or $R^2$ can be one, two or three groups such as $OR^7$, $SO_3M$, $COOR^8$ or $R^6$, with $R^6$ representing a $C_1$ to $C_6$ alkyl group optionally comprising from 1 to 5 oxygen atoms, $R^7$ representing a hydrogen atom or a $R^6$ group, M representing a hydrogen atom or an alkali metal ion, $R^8$ representing a M group or a $R^6$ group.

According to any one of the above embodiments of the invention, possible substituents of said $R^3$ or $R^5$ comprise one, two, three or four groups selected amongst ii) $C_{5-6}$ cycloalkyl groups, iii) $C_{1-6}$ alkoxy or alkyl groups, iv) $COOR^8$ wherein $R^8$ is as defined above, v) $CH_2OH$ or CHO groups, or vi) a benzyl group or a fused or non-fused phenyl or indanyl group, said group being optionally substituted by one, two or three halogen, $C_{1-8}$ alkyl, alkoxy, amino, ester, sulfonate or halo- or perhalo-hydrocarbon groups.

Alternatively, according to a further embodiment of the invention, the derivative of formula (I) is a compound wherein the various $R^1$, $R^2$, $R^3$ or $R^5$ are unsubstituted groups.

Alternatively, according to a further embodiment of the invention, the derivative of formula (I) is a compound of formula

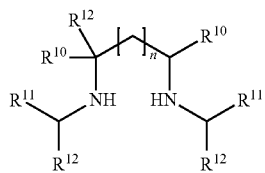

(II)

wherein n is 1 or 0, and each $R^{10}$ represents, independently of each other, a hydrogen atom, a phenyl group optionally substituted, or a $C_{1-4}$ alkyl group; when n is 0 the two $R^{10}$, taken together, may form a linear or branched $C_{3-6}$ alkanediyl group;

each $R^{11}$ represents, independently of each other, a $C_{3-5}$ heteroaryl group optionally substituted or one is a $C_{3-5}$ heteroaryl group optionally substituted and the other is a phenyl group optionally substituted; or one $R^{11}$ and one adjacent $R^{10}$ are taken together and represent a $C_{3-5}$ group forming with the carbon atoms to which they are linked and the NH group between them a saturated or a 1H-pyrrole ring which is optionally substituted; and each $R^{12}$ represents, independently of each other, a hydrogen atom or a methyl group.

Examples of possible substituents of said $R^{10}$ are one, two or three groups such as $OR^{7'}$, $SO_3M$, $COOR^{8'}$ or $R^{6'}$, with $R^{6'}$ representing a $C_{1-4}$ alkyl group optionally comprising from 1 to 2 oxygen atoms, $R^{7'}$ representing a hydrogen atom or a $R^{6'}$ group, M representing a hydrogen atom or an alkali metal ion, $R^{8'}$ representing a M group or a $R^{6'}$ group.

Examples of possible substituents of said $R^{11}$ comprise one or two selected amongst ii) $C_{5-6}$ cycloalkyl groups, iii) $C_{1-6}$ alkoxy or alkyl groups, iv) $COOR^8$ wherein $R^8$ is as defined above, v) $CH_2OH$ or CHO groups, or vi) a benzyl group or a fused or non-fused phenyl or indanyl group, said group being optionally substituted by one or two halogen, $C_{1-6}$ alkyl, alkoxy, amino, ester, sulfonate or perhalo-hydrocarbon groups.

According to any one of the above embodiments of the invention, said $R^{11}$ comprise one or two groups selected amongst iii) $C_{1-6}$ alkoxy or alkyl groups, iv) COOM wherein M is as defined above, v) $CH_2OH$ groups, or vi) a benzyl group or a fused or non-fused phenyl or indanyl group, said group being optionally substituted by one or two halogen, $C_{1-4}$ alkyl, alkoxy or amino groups.

According to any one of the above embodiments, $R^4$ or $R^{12}$ represents each a hydrogen atom.

According to any one of the above embodiments, $R^1$ or $R^{10}$ represents each a hydrogen atom or a phenyl group optionally substituted, or a methyl group. Or the two $R^1$, or the two $R^{10}$, when taken together, may form a linear $C_{3-4}$ alkanediyl group, in particular a $(CH_2)_4$ group.

According to any one of the above embodiments of the invention, said $R^1$, or $R^{10}$, are unsubstituted groups as defined in formula (II).

According to any one of the above embodiments, $R^3$ or $R^{11}$ represents each a $C_{3-5}$ heteroaryl group which is optionally substituted. For the sake of clarity it is understood that an heteroaryl group is an aromatic group comprising one or two heteroatoms, in particular oxygen, nitrogen or sulfur atoms. In particular said heteroatoms can be oxygen or nitrogen atoms.

According to any one of the above embodiments, and as non-limiting examples, said heteroaryl group (herein after also referred as to "Het") can be derived from furan, thiophene, 1H-pyrrole, pyridine groups (attached to the rest of the molecule via any of the carbon atoms of the heteroaryl group), and their substituted equivalents, as well as from benzofuran, benzo[b]thiophene, 1H-indole, and their substituted equivalents. Preferred substituents are methyl, phenyl or hydroxymethyl groups.

According to any one of the above embodiments, $R^3$ or $R^{11}$ represents each a $C_{3-5}$ 2-heteroaryl group as defined above.

According to any one of the above embodiments, said compound of formula (I) can be a compound of any of the formulae (III) to (VI)

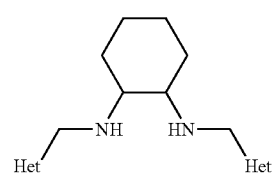

(III)

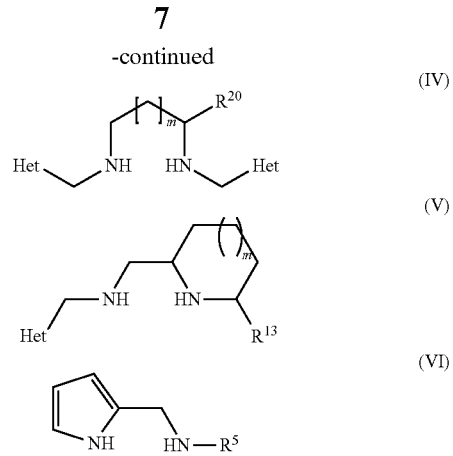

wherein m is 0 or 1, R⁵ is defined as described above, Het is a heteroaryl group as defined in any one of the above embodiments, R²⁰ represents a hydrogen atom or a $C_{1-3}$ alkyl group, R¹³ represents a hydrogen atom or a CH₂Het or CH₂NHCH₂Het group or an Alk group, Alk being a $C_{1-3}$ alkyl group optionally comprising a OH or COOM group, M being an alkali metal cation.

The diamine derivative of formula (V) is also a novel compound and therefore another aspect of the present invention. In particular, said compound (V) is one wherein m is 1 and R¹³ is a hydrogen atom. Preferred compounds of formula (V) are 1-(furan-2-yl)-N-(piperidin-2-ylmethyl)methanamine, 1-(piperidin-2-yl)-N-(thiophen-2-ylmethyl) methanamine, N-((1H-pyrrol-2-yl)methyl)-1-(piperidin-2-yl) methanamine and 1-(piperidin-2-yl)-N-(pyridin-2-, 3- or 4-ylmethyl)methanamine.

According to any one of the above embodiments, said compound of formula (I) can be a compound of formula (II), (III), (IV) or (V) and in particular of formula (III) or (IV).

As non limiting examples of diamines, one may cite the following: N,N'-bis(2-furanylmethyl)cyclohexane-1,2-diamine, N,N'-bis(pyridin-2-, 3- or 4-ylmethyl)cyclohexane-1,2-diamine, N,N'-bis((1H-pyrrol-2-yl)methyl)cyclohexane-1,2-diamine, N,N'-bis((5-methylfuran-2-yl)methyl) cyclohexane-1,2-diamine, (5,5'-((cyclohexane-1,2-diylbis (azanediyl))bis(methylene))bis(furan-5,2-diyl))dimethanol, N,N'-bis(furan-2-ylmethyl)ethane-1,2-diamine, N,N'-bis(furan-2-ylmethyl)propane-1,2-diamine, N,N'-bis(furan-2-ylmethyl)propane-1,3-diamine, N,N'-bis(pyridin-2-, 3- or 4-ylmethyl)ethane-1,2-diamine, N,N'-bis(pyridin-2-, 3- or 4-ylmethyl)propane-1,3-diamine, N,N'-bis((1H-pyrrol-2-yl) methyl)ethane-1,2-diamine, N,N'-bis((1H-pyrrol-2-yl)methyl)propane-1,3-diamine, 1-(furan-2-yl)-N-(piperidin-2-ylmethyl)methanamine, N-((1H-pyrrol-2-yl)methyl)-1-(piperidin-2-yl)methanamine, 1-(piperidin-2-yl)-N-(thiophen-2-ylmethyl)methanamine, and 1-(piperidin-2-yl)-N-(pyridin-2-, 3- or 4-ylmethyl)methanamine.

According to some specific embodiments, the diamines N,N'-bis(2-furanylmethyl)cyclohexane-1,2-diamine, N,N'-bis(furan-2-ylmethyl)ethane-1,2-diamine, N,N'-bis(furan-2-ylmethyl)propane-1,2-diamine and N,N'-bis(furan-2-ylmethyl)propane-1,3-diamine are particularly suitable.

Furthermore, the compounds of formula (I) may be in their protonated or unprotonated form. Examples of protonated forms are those obtained by the addition of a proton to at least one of the —NHR³ groups to form a —NH₂R³⁺ moiety. Compounds of this type include in particular hydrochloride or hydrobromide derivatives of the compounds according to formula (I). Protonation and deprotonation is dependent on the pH of the medium, under highly acidic conditions for example compounds of formula (I) are expected to be in their protonated form.

Furthermore, in all the above-mentioned embodiments of the invention, the derivatives of formula (I) which are odorless, i.e. do not possess a significant odor themselves, or are even essentially non-volatile (i.e. possesses a vapor pressure of below about 150 mPa, preferably below 11 mPa, as obtained by calculation using the software EPIwin v 3.10, available at 2000 US Environmental Protection Agency) represent particularly appreciated examples.

Another important constituent of the invention's dynamic mixture are the perfuming compounds. Examples of perfuming aldehydes or ketones are available in perfumery handbooks or in the specialized literature or in the art patents, as mentioned further below.

Said perfuming compounds comprise, preferably, between 5 and 15 carbon atoms.

According to an embodiment of the invention, said perfuming aldehydes or ketones have a molecular weight comprised between 90 and 200 g/mol and can be advantageously selected from the group consisting of an enal, an enone, an aldehyde comprising the moiety CH₂CHO or CHMeCHO, an aryl aldehyde or aryl ketone (i.e. an aldehyde or ketone wherein the carbonyl functional group is directly bound to an aryl ring) and a cyclic or acyclic ketone (wherein the CO group is part or not of a cycle).

In particular, said perfuming aldehyde can be an aldehyde comprising the moiety CH₂CHO or CHMeCHO (i.e. the CHO group is not directly linked to a cyclic group).

Furthermore, according to any of the embodiments mentioned above, said perfuming aldehydes or ketones are advantageously characterized by a vapor pressure comprised between above about 2.0 Pa, or preferably 5.0, or even more preferably 7.0 Pa, and below about 450 Pa, or preferably 40, or even more preferably 35 Pa, as obtained by calculation using the software EPIwin v 3.10 (available at 2000 US Environmental Protection Agency). In particular, said vapor pressure can be comprised between above about 7.0 Pa, and below about 35 Pa.

More specifically, as non-limiting examples of the perfuming compounds in the embodiments mentioned above, one may cite the following:

A) aldehydes of formula R"'—CHO wherein R"' is a linear or α-branched alkyl group of $C_6$ to $C_{12}$, benzaldehyde, 1,3-benzodioxol-5-carboxaldehyde (heliotropine), 3-(1,3-benzodioxol-5-yl)-2-methylpropanal, 2,4-decadienal, 2-decenal, 4-decenal, 8-decenal, 9-decenal, 3-(6,6-dimethyl-bicyclo[3.1.1]hept-2-en-2-yl)propanal, 2,4-dimethyl-3-cyclohexene-1-carbaldehyde (Triplal®, origin: International Flavors & Fragrances, New York, USA), 3,5-dimethyl-3-cyclohexene-1-carbaldehyde, 1-(3,3-dimethyl-1-cyclohexyl)-1-ethanone, 5,9-dimethyl-4,8-decadienal, 2,6-dimethyl-5-heptenal (melonal), 3,7-dimethyl-2,6-octadienal (citral), 3,7-dimethyloctanal, 3,7-dimethyl-6-octenal (citronellal), (3,7-dimethyl-6-octenyl) acetaldehyde, 3-dodecenal, 4-dodecenal, 3-ethoxy-4-hydroxybenzaldehyde (ethyl vanillin), 4-ethyl benzaldehyde, 3-(2 and 4-ethylphenyl)-2,2-dimethylpropanal, 2-furancarbaldehyde (furfural), 2,4-heptadienal, 4-heptenal, 2-hexenal, 2-hexyl-3-phenyl-2-propenal (hexylcinnamic aldehyde), 2-hydroxybenz aldehyde, 7-hydroxy-3,7-dimethyloctanal (hydroxycitronellal), 4-hydroxy-3-methoxybenzaldehyde (vanillin), 4- and 3-(4-hydroxy-4-methylpentyl)-3-cyclohexene-1-carbaldehyde (Lyral®, origin: International Flavors and Fragrances, New York, USA), 4-isopropylbenzaldehyde (cuminaldehyde), 8-isopropyl-6-methyl-bicyclo[2.2.2] oct-5-ene-2-carbaldehyde, 3-(4-isopropylphenyl)-2-methylpropanal, 2-(4-isopropylphenyl)propanal, 1,8-p-menthadien-7-al, (4R)-1-p-menthene-9-carbaldehyde (Liminal®, origin: Firmenich S A, Geneva, Switzerland), 2- and 4-methoxybenzaldehyde (anis aldehyde), 6-methoxy-2,6-dimethylheptanal (methoxymelonal), 3-(2-methoxyphenyl)acrylaldehyde, 8(9)-methoxy-tricyclo[5.2.1.0.(2,6)]decane-3(4)-carbaldehyde (Scentenal®, origin: Firmenich S A, Geneva, Switzerland), 4-methylbenzaldehyde, 2-(4-methylenecyclohexyl)propanal, 1-methyl-4-(4-methyl-3-pentenyl)-3-cyclohexen-1-carbaldehyde (Precyclemone® B, origin: International Flavors & Fragrances, New York, USA), 4-(4-methyl-3-pentenyl)-3-cyclohexene-1-carbaldehyde (Acropal®, origin: Givaudan-Roure S A., Vernier, Switzerland), (4-methylphenoxy)acetaldehyde, (4-methylphenyl) acetaldehyde, 3-methyl-5-phenylpentanal, 2-(1-methylpropyl)-1-cyclohexanone, 2,4-nonadienal, 2,6-nonadienal, 2-nonenal, 6-nonenal, 8-nonenal, 2-octenal, 2-pentyl-3-phenyl-2-propenal, phenoxyacetaldehyde, phenylacetaldehyde, 3-phenylbutanal (Trifernal®, origin: Firmenich S A, Geneva, Switzerland), 3-phenylpropanal, 2-phenylpropanal (hydratropaldehyde), 3-phenyl-2-propenal (cinnamic aldehyde), 3-(4-tert-butylphenyl)-2-methylpropanal (Lilial®, origin: Givaudan-Roure S A, Vernier, Switzerland), 3-(4-tert-butylphenyl)propanal (Bourgeonal®, origin: Quest International, Naarden, Netherlands), tricyclo[5.2.1.0(2,6)]decane-4-carbaldehyde, exo-tricyclo[5.2.1.0(2,6)]decane-8exo-carbaldehyde (Vertral®, origin: Symrise, Holzminden, Germany), 2,6,6-trimethyl-bicyclo[3.1.1] heptane-3-carbaldehyde (formyl pinane), 2,4,6- and 3,5,6-trimethyl-3-cyclohexene-1-carbaldehyde, 2,2,3-trimethyl-3-cyclopentene-1-acetaldehyde (campholenic aldehyde), 2,6,10-trimethyl-2,6,9,11-dodecatetraenal, 2,5,6-trimethyl-4-heptenal, 3,5,5-trimethylhexanal, 2,6,10-trimethyl-9-undecenal, 2-undecenal, 10-undecenal or 9-undecenal and their mixtures such as Intreleven aldehyde (origin: International Flavors & Fragrances, New York, USA), and B) $C_{6-11}$ ketones of formula R'—(CO)—R" wherein R' and R" are linear alkyl groups, damascenones and damascones, ionones and methyl ionones (such as Iralia® Total, origin: Firmenich S A, Geneva, Switzerland), irones, macrocyclic ketones such as, for example, cyclopentadecanone (Exaltone®) or 3-methyl-4-cyclopentadecen-1-one and 3-methyl-5-cyclopentadecen-1-one (Delta Muscenone) or 3-methyl-1-cyclopentadecanone (Muscone) all from Firmenich S A, Geneva, Switzerland, 1-(2-aminophenyl)-1-ethanone, 1-(5,5-dimethyl-1-cyclohexen-1-yl)-4-penten-1-one (Neobutenone®, origin: Firmenich S A, Geneva, Switzerland), 1-(3,3-dimethyl-1-cyclohexyl)-1-ethanone, 2,5-dimethyl-2-octene-6-one, 4,7-dimethyl-6-octene-3-one, (3,7-dimethyl-6-octenyloxy)acetaldehyde, 1-(2,4-dimethylphenyl)-1-ethanone, 4-(1,1-dimethylpropyl)-1-cyclohexanone (Orivone®, origin: International Flavors & Fragrances, New York, USA), 2,4-di-tert-butyl-1-cyclohexanone, ethyl 4-oxopentanoate, 1-(4-ethylphenyl)-1-ethanone, 2-hexyl-1-cyclopentanone, 2-hydroxy-3-methyl-2-cyclopenten-1-one, 4-(4-hydroxy-1-phenyl)-2-butanone (raspberry ketone), 1-(2- and 4-hydroxyphenyl)-1-ethanone, 4-isopropyl-2-cyclohexen-1-one, 1-(4-isopropyl-1-phenyl)-1-ethanone, 1(6), 8-p-menthadien-2-one (carvone), 4(8)-p-menthen-3-one, 1-(1-p-menthen-2-yl)-1-propanone, menthone, (1R,4R)-8-mercapto-3-p-menthanone, 1-(4-methoxyphenyl)-1-ethanone, 7-methyl-2H,4H-1,5-benzodioxepin-3-one (Calone®, origin: C.A.L. S A, Grasse, France), 5-methyl-3-heptanone, 6-methyl-5-hepten-2-one, methyl 3-oxo-2-pentyl-1-cyclopentaneacetate (Hedione®, origin: Firmenich S A, Geneva, Switzerland), 1-(4-methylphenyl)-1-ethanone (4-methylacetophenone), 5-methyl-exo-tricyclo[6.2.1.0(2,7)]undecan-4-one, 3-methyl-4-(1,2,2-trimethylpropyl)-4-penten-2-one, 2-naphthalenyl-1-ethanone, 1-(octahydro-2,3,8,8-tetrame-2-naphthalenyl)-1-ethanone (isomeric mixture, Iso E Super®, origin: International Flavors & Fragrances, New York, USA), 3,4,5,6,6-pentamethyl-3-hepten-2-one, 2-pentyl-1-cyclopentanone (Delphone, origin: Firmenich S A, Geneva, Switzerland), 4-phenyl-2-butanone (benzylacetone), 1-phenyl-1-ethanone (acetophenone), 2- and 4-tert-butyl-1-cyclohexanone, 1-(4-tert-butylphenyl)-1-ethanone), 2,4,4,7-tetramethyl-6-octen-3-one, 1,7,7-trimethyl-bicyclo[2.2.1]heptan-2-one (camphor), 2,6,6-trimethyl-1-cycloheptanone, 2,6,6-trimethyl-2-cyclohexene-1,4-dione, 4-(2,6,6-trimethyl-2-cyclohexen-1-yl)-2-butanone (dihydroionone), 1-(2,4,4-trimethyl-2-cyclohexen-1-yl)-2-buten-1-one, 1-(3,5,6-trimethyl-3-cyclohexen-1-yl)-1-ethanone, 2,2,5-trimethyl-5-pentyl-1-cyclopentanone;

wherein the underlined compounds represent, in an embodiment of the invention, particularly useful fragrance aldehydes or ketones.

As mentioned above, according to an embodiment of the invention, perfuming aldehydes are preferably used.

Furthermore, in all the aspects of the above-described invention, the delivery systems may further comprise other amine derivatives known to generate dynamic mixtures, and in particular the diamines described in WO 08/093,272, e.g. the N,N'-dibenzyl-1,2- or 1,3-diamine derivatives.

The invention's dynamic mixture can be obtained by admixing together, in the presence of water, at least one invention's diamine and at least two perfuming compounds. It is very frequent in the perfumery art to admix together several perfumery ingredients to achieve a more pleasant and natural scent. However, it must be considered that every single compound present in a dynamic mixture may influence the overall equilibrium and therefore the evaporation of every single perfuming ingredient. Under such circumstances, one could have expected that the presence of several compounds capable of reacting all together (each of them with different stabilities and reactivities), could have easily led to a negative impact of the release of the individual perfuming aldehyde or ketone. This could result in a negative hedonic effect, or at least (and in the best case) that only some particular perfuming ingredients would be boosted, resulting in any case in a modification of the olfactive profile of the perfume over time, which is obviously an undesired result. Now, to the contrary of the expectation and very surprisingly, we found that the use of a diamine according to the present invention provides a general improvement of performance of all aldehydes and ketones in a mixture and that this improved performance is more evenly distributed between the different carbonyl compounds in the mixture.

Therefore, in all the aspects of the above-described invention, a dynamic mixture obtained by reacting together at least one derivative of formula (I) with at least two, or even at least five, ten or fifteen, perfuming compounds is particularly appreciated. Similarly, in all the aspects of the above-described invention, it is also particularly appreciated to obtain a dynamic mixture by reacting together at least one or two derivatives of formula (I) with at least two, or even at least five, ten or fifteen, perfuming compounds.

As mentioned above, the invention's dynamic mixture comprises several starting components that may react, in a reversible manner, between them to form addition products.

Now, a further aspect of the present invention concerns the dynamic mixtures themselves. Indeed, the above-mentioned dynamic mixtures are also new, and therefore represent another object of the invention. So another aspect of the present invention are the dynamic mixtures as such, useful for the controlled release of perfuming aldehydes or ketones. In particular said dynamic mixture are consisting of the aqueous medium, in particular water at an appropriate pH, the invention's diamine, the perfuming compound and the reaction product of said last two ingredients.

It is believed that the main components of the dynamic mixture are the free aldehyde and/or ketone, the invention's diamine and the resulting addition products (such as the corresponding aminal derivatives). A specific example of such a mixture and equilibrium is presented in Scheme (I):
Scheme (I): Example of an equilibrium and the species present in a dynamic mixture obtained from one specific aldehyde and one specific diamine derivative or from the corresponding aminal derivative wherein n, $R^1$, $R^2$, $R^3$, $R^4$ and $R^5$ have the meaning as described above and $R^{14}$ and $R^{15}$ are the residues derived from a perfuming aldehyde (if $R^{15}$ is a hydrogen atom) or ketone (if $R^{14}$ and $R^{15}$ are substituted or unsubstituted hydrocarbon groups) of formula $R^{14}(C=O)R^{15}$, said aminal being obtainable by a process comprising reacting together
- a diamine of formula (I), as defined above, preferably having a molecular weight equal to or above 180 g/mol or even above 230 g/mol; and
- a perfuming aldehyde or ketone $R^{14}(C=O)R^{15}$ having a molecular weight comprised between 80 and 230 g/mol, in particular being selected from the group consisting of the $C_{5-20}$ perfuming aldehydes and the $C_{5-20}$ perfuming ketones. Preferred compounds are those with $R^{15}$ being a hydrogen atom.

According to a particular embodiment of the invention, said aminals of formula (VII) are those wherein the perfuming aldehyde or ketone $R^{14}(C=O)R^{15}$ is one of those mentioned above. Yet according to another particular embodiment said $R^{15}$ is a hydrogen atom and said $R^{14}$ can be defined as $R^{16}$ herein below.

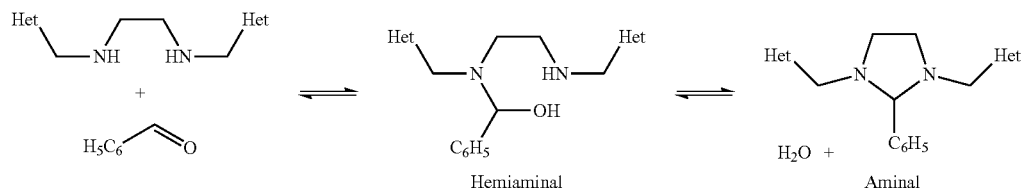

Hemiaminal    Aminal

As a consequence of the fact that the reactions are reversible, a dynamic mixture can also be obtained by adding several aminal derivatives, or by adding one aminal derivative and one perfuming compound into water and letting the mixture attain its equilibrium. However, it has to be pointed out that the time required to reach the equilibrium point can vary significantly depending on the fact that there is used, for instance, the invention's diamine as starting material, as said time is believed to be dependent on various parameters such as solubilities or the pH of the medium.

The preparation of the invention's dynamic mixture by the simple admixture of the perfuming compounds and of at least one invention's diamine in the presence of water avoids the need of additional chemical steps such as the preparation of the corresponding aminal, and is therefore a preferred method.

Furthermore, since the aminals can also be used as precursors of the dynamic mixtures, another aspect of the invention concerns the use of said aminals as precursors of the invention's dynamic mixtures, or the use of said aminals for prolonging the perfuming effect of a perfuming aldehyde or ketone. Said aminals are of formula (VII)

Furthermore, since some of the above aminals (VII) are also new compounds, another aspect of the invention concerns said aminals as such. Said new aminals according to the invention are of formula (VIII)

(IX)

(X)

wherein m is 0 or 1, Het is a heteroaryl group as above defined, Alk is a $C_{1-3}$ alkyl group, $R^{20}$ represents a hydrogen atom or a $C_{1-3}$ alkyl group, and $R^{16}$ is the residue of a perfuming aldehyde $R^{16}CHO$ having a molecular weight comprised between 80 and 230 g/mol and being a perfuming ingredient, and wherein $R^{16}$ represents a $C_6$-$C_{14}$ alkyl, alkenyl or alkadienyl group optionally comprising one, two or three oxygen atoms, or a $C_{1-4}$ alkyl or alkenyl group substituted by a phenyl group optionally substituted by one, two or three OH, $R^{17}$ or $OR^{17}$ groups, $R^{17}$ being an acetyl or a $C_1$-$C_4$ alkyl or alkenyl group.

According the above embodiments, said $R^{16}$CHO is an aldehyde wherein said $R^{16}$ represents a $CH_2R^{18}$ or $CHMeR^{18}$ group, $R^{18}$ representing a $C_{4-13}$ hydrocarbon group optionally comprising one, two or three oxygen atoms.

Due to its nature, the invention's dynamic mixture circumvents the problem of product instability observed with prior art precursors, by the fact that a dynamic equilibrium is spontaneously set up between these compounds. This instability problem is avoided in a way significantly different from the one described in the prior art (e.g. in DE 10-2005-062175 A1) where it is always mentioned that it is preferable to increase as much as possible the degradation of the aminals against hydrolysis. In the case of the present invention, the equilibrium is stable during product storage as long as the consumer product parameters (such as concentration, temperature, pH or humidity, the presence of surfactant, etc.) are kept constant. At a given set of parameters, the time required to reach the equilibrium state mainly depends on the kinetic rate constant of the slowest step involved in the formation of the products of the equilibrium.

The invention's dynamic mixture is furthermore able to stabilize perfuming aldehydes and ketones, against degradation, in aqueous media by reversibly forming an addition product between a compound of formula (I) and the perfuming aldehyde or ketone and thus reversibly protect the carbonyl function as an aminal function, for example of formula (VII). The spontaneous reversible formation of a high amount of aminals in the dynamic mixture is thus expected to stabilize the carbonyl functionality of the perfuming aldehyde or ketone to a large extent.

As mentioned above, the dynamic mixture of the invention comprises various components. It is believed that, once the dynamic mixture is deposited on a surface, the free perfuming aldehydes or ketones start to evaporate, diffusing in the surrounding environment their typical scent. Said evaporation perturbs the chemical equilibrium and the various addition products start to decompose so as to restore the equilibrium. The consequence of such re-equilibration is the regeneration of free perfuming aldehydes or ketones, thus maintaining their concentration relatively constant over time and avoiding a too rapid evaporation.

Now, it has been observed that the various physical or thermodynamic properties of the dynamic mixture, e.g. its deposition on a surface or the amount of addition products formed, can be influenced by the chemical nature of the perfuming compounds or of the derivatives of formula (I). Another way to influence the above-mentioned properties is to modify the molar ratio between said perfuming compounds and the derivatives of formula (I). For instance, the lower the molar ratio between perfuming compounds and derivatives of formula (I), the longer takes the evaporation of all the perfuming compounds. The presence of other ingredients (such as surfactants, emulsifiers, gelators or others) typically used in the final consumer product formulation may also influence the above-mentioned properties.

Therefore, by varying the chemical structure of the mixture's constituents and their ratio, it is possible to fine-tune the release properties of the invention's dynamic mixture, so as to adapt its behavior to the specific requirement of the targeted consumer product.

According to the final application, a broad range for the speed of evaporation of the perfuming compounds may be desirable.

The ratio between the total molar amount of perfuming compounds and the total molar amount of the compound of formula (I) can be comprised between 1:2 and 50:1, preferably between 1:1 and 10:1.

The amount of free perfuming compounds present in the equilibrated dynamic mixture is comprised between 1 and 97%, preferably between 5 and 95% or even more preferably between 25 and 90%.

Another advantage of the invention resides in the fact that it is possible to fine-tune the thermodynamic behavior of the dynamic mixture by selecting the nature of the $R^1$ to $R^5$ groups. It is therefore conceivable to design dynamic mixtures comprising, for instance, a derivative of formula (I) which allows a fast release of a specific perfuming aldehyde (which will be perceivable at the beginning of the consumer use only) and a second derivative of formula (I) which allows a release of the same specific aldehyde, or of another, a very slow release (which will be perceivable even after an important delay from the direct consumer use).

Moreover, another object of the present invention concerns also a composition comprising the invention's dynamic mixture. This concerns also in particular a perfuming composition comprising:
i) as perfuming ingredient, a dynamic mixture as defined above;
ii) at least one ingredient selected from the group consisting of a perfumery carrier and a perfumery base; and
iii) optionally at least one perfumery adjuvant.

Preferably, in said perfuming composition the perfumery carrier, perfumery base and perfumery adjuvant have a total molar amount of aldehydes or ketones which is equal to or higher than the molar amount of derivatives of formula (I) of the dynamic mixture.

By "perfumery carrier" we mean here a material which is practically neutral from a perfumery point of view, i.e. that does not significantly alter the organoleptic properties of perfuming ingredients. Said carrier may be a liquid. As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as ethanol, dipropyleneglycol, diethyl phthalate, isopropyl myristate, benzyl benzoate, 2-(2-ethoxyethoxy)-1-ethanol or ethyl citrate, which are the ones most commonly used.

By "perfumery base" we mean here a composition comprising at least one perfuming co-ingredient. Said perfuming co-ingredient is not an aldehyde or ketone as defined above for the dynamic mixture. Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, esters, lactones, ethers, acetates, nitriles, terpene hydrocarbons, nitrogenous or sulphurous heterocyclic compounds and essential oils, and said perfuming co-ingredients can be of natural or synthetic origin. A further class of perfuming co-ingredients can be the aldehydes or ketones which do not react with the diamine derivative present in the dynamic mixture.

Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability (e.g. antioxidants) and others. A detailed description of the nature and type of adjuvant commonly used in perfuming bases cannot be exhaustive, but it has to be mentioned that said ingredients are well known to a person skilled in the art.

An invention's composition consisting of an invention's dynamic mixture and at least one perfumery carrier represents a particular embodiment of the invention as well as a perfuming composition comprising an invention's dynamic mixture, at least one perfumery carrier, at least one perfumery base, and optionally at least one perfumery adjuvant.

As anticipated above, the invention's dynamic mixtures or compositions can be advantageously used for bringing a benefit to consumer products, such as its perfuming effect. Because some of the volatile $C_{5-20}$ perfuming aldehydes and $C_{5-20}$ perfuming ketones described above can also have insect attractant or repellent, bactericide, fungicide or malodor counteracting properties, it is evident that the invention's dynamic mixture can also be used in formulations serving for insect attractant or repellent, bactericide, fungicide or malodor counteracting purposes. Indeed, said mixture possesses several other properties that make it particularly suitable for this purpose. Consequently, a consumer article comprising the invention's dynamic mixture is also an object of the present invention.

Indeed, and for example, another advantage of the invention's mixture is an improved deposition on a surface of the perfuming aldehydes or ketones compared to those of the pure aldehydes or ketones as such.

All the above-mentioned properties, i.e., improved substantivity, prolonged time of evaporation, improved stability over aggressive agents and improved deposition, are very important for a perfuming composition. Indeed, when said compositions are intended for use in fine perfumery, the invention's mixture may allow the creation of new perfuming effects which are otherwise difficult to be achieved, such as a fresh green note being present over several hours. In the case of perfuming compositions intended for the functional perfumery, the above-mentioned properties are also very important. For example, perfuming ingredients present as such in washing compositions which have generally little staying-power on a surface are consequently often eliminated, for example in the rinsing water or upon drying of said surface.

This problem can be solved by using the invention's dynamic mixture, which possesses an improved stability over storage and substantivity on surfaces, such as textiles or hair.

Therefore, the mixtures according to the invention, owing to a lower and more uniform evaporation per unit of time, resulting in a controlled release of odoriferous molecules, can be incorporated in any application requiring the effect of prolonged liberation of an odoriferous component as defined hereinabove and furthermore can impart a fragrance and a freshness to a treated surface which will last well beyond the rinsing and/or drying processes. Suitable surfaces are, in particular, textiles, hard surfaces, hair and skin.

Consequently, the invention concerns also a liquid perfuming consumer product which comprises:
i) as perfuming ingredient, a dynamic mixture as defined above; and
ii) a liquid perfumery consumer base.

Preferably, in perfumed articles, the liquid perfumery consumer base has a total molar amount of aldehydes and/or ketones which is equal to or higher than the molar amount of derivatives of formula (I) of the dynamic mixture.

For the sake of clarity, it has to be mentioned that, by "liquid perfuming consumer product", it is meant a consumer product which is expected to deliver at least a perfuming effect and which is not a solid, e.g. a more or less viscous solution, a suspension, an emulsion, a gel or a cream. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactively effective amount of an invention's dynamic mixture.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent. As "detergents" are intended consumer product bases such as detergent compositions or cleaning products for washing up or for cleaning various surfaces, e.g. intended for textile, dish or hard-surface treatment, whether they are intended for domestic or industrial use.

Preferred consumer products are perfumes, air fresheners, deodorants or antiperspirants, soaps, cosmetic preparations, ironing waters, detergents (for home or body care), fabric softeners, fabric refreshers, shampoos or hair sprays.

Even more preferred consumer products are detergents, softener bases or fabric refreshers, liquid based deodorants or antiperspirants or air fresheners comprising a liquid perfuming ingredient.

According to an embodiment of the invention, it is also possible to have a perfumed article comprising:
i) a derivative of formula (I), as described above, and/or at least one aminal obtainable from a derivative of formula (I) and a perfuming aldehyde or ketone as above defined; and a perfume or perfuming composition containing at least one perfuming aldehyde or ketone having a molecular weight comprised between 80 and 230 g/mol; or
at least one aminal obtainable from a derivative of formula (I) and a perfuming aldehyde or ketone as above defined; and
ii) a solid consumer product base intended to be used in the presence of water.

In such a case, the invention's dynamic mixture will be formed once the consumer article is used by the consumer, since water will be present. Examples of such solid consumer product bases intended to be used in the presence of water include powder detergents or "ready to use" powdered air fresheners. In particular, the aminals cited above can be one of formula (VII).

Typical examples of fabric detergents or softener compositions into which the compounds of the invention can be incorporated are described in Ullman's Encyclopedia of Industrial Chemistry, vol. A8, pages 315-448 (1987) and vol. A25, pages 747-817 (1994); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

Some of the above-mentioned articles may represent an aggressive medium for the invention's compounds, so that it may be necessary to protect the latter from premature decomposition, for example by encapsulation.

The proportions in which the dynamic mixture according to the invention can be incorporated into the various aforementioned articles or compositions vary within a wide range of values. These values are dependent on the nature of the article or product to be perfumed and on the desired olfactory effect as well as the nature of the co-ingredients in a given composition when the dynamic mixtures according to the invention are mixed with perfuming co-ingredients, solvents or additives commonly used in the art. For example, typical concentrations are in the order of 0.1% to 30% by weight, or even more, of the invention's dynamic mixture based on the weight of the composition into which they are incorporated. Concentrations lower than these, such as in the order of 0.01% to 5% by weight, can be used when these dynamic mixtures are applied directly in the perfuming of the various consumer products mentioned hereinabove.

Another object of the present invention relates to a method for the perfuming of a surface characterized in that said surface is treated in the presence of a dynamic mixture as defined above. Suitable surfaces are, in particular, textiles, hard surfaces, hair and skin.

Moreover, an additional aspect of the present invention is a method for prolonging the perfuming effect of a perfuming aldehyde or ketone, as defined above, characterized in that at least one derivative of formula (I), as defined above, is added to a perfuming composition or perfumed article containing at least one of said aldehyde or ketone and water. In other words, it concerns the use of a derivative of formula (I), as defined above, as additive to prolong the perfuming effect of a perfuming compositions or perfumed article containing at least two perfuming compounds as defined above and water.

EXAMPLES

The invention will now be described in further detail by way of the following examples, wherein the abbreviations have the usual meaning in the art, the temperatures are indicated in degrees centigrade (° C.). If not stated otherwise, the NMR spectral data were recorded on a Bruker AMX 400 spectrometer in $CDCl_3$ or DMSO-$d_6$ at 400 MHz for $^1H$ and at 100.6 MHz for $^{13}C$, the chemical displacements δ are indicated in ppm with respect to TMS as the standard, the coupling constants J are expressed in Hz (br.=broad peak). Commercially available reagents and solvents were used without further purification if not stated otherwise. Reactions were carried out in standard glassware under $N_2$.

Although specific conformations or configurations are indicated for some of the compounds, this is not meant to limit the use of these compounds to the isomers described. According to the invention, all possible conformation or configuration isomers are expected to have a similar effect.

The following primary diamine derivatives used as the starting materials for the preparation of secondary diamines were obtained from commercial sources (some of which might be sold as their corresponding hydrochloride salts): (cis/trans)-1,2-diaminocyclohexane (origin: Aldrich), (1RS, 2RS)-1,2-diaminocyclohexane (origin: Alfa Aesar), (1RS, 2SR)-1,2-diaminocyclohexane (origin: Fluka), (cis/trans)-1, 3-diaminocyclohexane (cis/trans ca. 2.5:1, origin: TCI), (1R, 2S)-1,2-diphenylethane-1,2-diamine (origin: Aldrich), 2-(aminomethyl)piperidine (origin: Wako), 1,2-diaminoethane (origin: Acros), 1,3-diaminopropane (origin: Acros) and aminocyclohexane (origin: Acros).

Non commercial diamines according to the invention were prepared as follows:
General method for the preparation of secondary diamines (Method A)

The carboxaldehyde was added to a solution of the primary diamine in methanol (10 or 20 mL). The reaction mixture was stirred at 70° C. for 15-18 h. Then the reflux was stopped and $NaBH_4$ (0.40 g, 10.6 mmol) was added in small portions during 10 min After heating at reflux for 2-4 h, the mixture was cooled to room temperature and the solvent was evaporated. The residue was taken up with HCl (10% aqueous solution, 10 or 20 mL) and washed with ethyl acetate (10 or 20 mL, 2×). In some cases more ethyl acetate was added to facilitate the phase separation. The aqueous phase was separated, then NaOH (10% aqueous solution, 15 or 25 mL) was added and the mixture extracted with ethyl acetate (10 or 20 mL, 3×). The assembled organic phases were dried ($Na_2SO_4$) and the solvent evaporated. Drying under vacuum gave the desired diamine.

General method for the preparation of secondary diamines (Method B)

A solution of the primary diamine in ethanol (10 mL) was added dropwise to a solution of the carboxaldehyde in ethanol (10 mL). The reaction mixture was stirred at reflux for 1-2 h. Then the reflux was stopped and $NaBH_4$ was added in small portions. After heating at reflux for another 5 h, the mixture was cooled to room temperature and the solvent was evaporated. The residue was taken up with demineralized water and extracted with chloroform (10-20 mL, 3×). The assembled organic phases were dried ($Na_2SO_4$) and the solvent evaporated. Drying under vacuum gave the desired diamine

Synthesis of (1RS,2RS)—N,N'-bis(2-furanylmethyl)cyclohexane-1,2-diamine [(trans)-N,N'-bis(2-furanylmethyl)cyclohexane-1,2-diamine]

This compound was prepared as described in the general method (Method A) with furan-2-carboxaldehyde (furfural, 1.68 g, 17.5 mmol) and (1RS,2RS)-1,2-diaminocyclohexane (1.00 g, 8.8 mmol) to give 2.18 g (91%) of the desired diamine.

$^1$H-NMR (DMSO-$d_6$): 7.52 (dd, J=1.8, 1.0 Hz, 2 H); 6.35 (dd, J=3.1, 1.8 Hz, 2 H); 6.20 (dd, J=3.2, 0.7 Hz, 2 H); 3.73 (d, J=14.8 Hz, 2 H); 3.58 (d, J=14.6 Hz, 2 H); 2.27-2.05 (m, 4 H); 2.02-1.90 (m, 2 H); 1.72-1.51 (m, 2 H); 1.20-1.02 (m, 2 H); 1.02-0.86 (m, 2 H).

$^{13}$C-NMR (DMSO-$d_6$): 154.89 (s); 141.52 (d); 110.12 (d); 106.06 (d); 59.87 (d); 42.71 (t); 30.45 (t); 24.47 (t).

Using the same procedure and product quantities, (1RS,2SR)—N,N'-bis(2-furanylmethyl)cyclohexane-1,2-diamine [(cis)-N,N'-bis(2-furanylmethyl)cyclohexane-1,2-diamine] was prepared from (1RS,2SR)-1,2-diaminocyclohexane and furfural to give 2.03 g (84%) of the desired diamine.

$^1$H-NMR (DMSO-$d_6$): 7.53 (dd, J=1.8, 0.8 Hz, 2 H); 6.34 (dd, J=3.1, 1.8 Hz, 2 H); 6.19 (dd, J=3.1, 0.5 Hz, 2 H); 3.61 (d, J=14.6, 2 H); 3.53 (d, J=14.6, 2 H); 2.64-2.58 (m, 2 H); 2.07 (br. s, 2 H); 1.65-1.48 (m, 4 H); 1.27-1.11 (m, 4 H).

$^{13}$C-NMR (DMSO-$d_6$): 154.71 (s); 141.64 (d); 110.15 (d); 106.40 (d); 54.64 (br. d); 42.63 (t); 27.20 (t); 21.92 (br. t).

Similarly, using the same procedure and product quantities, (cis/trans)-N,N'-bis(2-furanylmethyl)cyclohexane-1,2-diamine was prepared from (cis/trans)-1,2-diaminocyclohexane and furfural to give 1.79 g (75%) of the desired diamine

Synthesis of (cis/trans)-N,N'-bis((5-methylfuran-2-yl)methyl)cyclohexane-1,2-diamine This compound was prepared as described in the general method (Method A) with 5-methylfurfural (1.93 g, 17.6 mmol) and (cis/trans)-1,2-diaminocyclohexane (1.00 g, 8.8 mmol) to give 2.21 g (83%) of the desired diamine.

$^1$H-NMR (DMSO-$d_6$): 6.08-6.02 (m, 2 H); 5.96-5.92 (m, 2 H); 3.67 and 3.54 (d, J=14.4 and 14.6 Hz, 2 H); 3.50 and 3.45 (d, J=14.4 and 14.5 Hz, 2 H); 2.64-2.57 and 2.15-2.06 (m, 2 H); 2.19 (s, 6 H); 2.02-1.90 and 1.67-1.48 (m, 4 H); 1.26-1.08 and 1.01-0.84 (m, 4 H).

$^{13}$C-NMR (DMSO-$d_6$): 153.05 and 152.83 (s); 150.08 and 149.96 (s); 107.05 and 106.73 (d); 105.97 (d); 59.87 and 54.61 (br.) (d); 42.83 and 42.69 (t); 30.52 and 27.18 (t); 24.51 and 21.92 (br.) (t); 13.17 (q).

Synthesis of (cis/trans)-(5,5'-((cyclohexane-1,2-diylbis(azanediyl))bis(methylene))bis (furan-5,2-diyl)) dimethanol This compound was prepared as described in the general method (Method A) with 5-hydroxymethylfurfural (2.21 g, 17.6 mmol) and (cis/trans)-1,2-diaminocyclohexane (1.00 g, 8.8 mmol). Drying under vacuum (30 min and 60° C., 2 h) gave 2.18 g (74%) of the desired diamine, still containing some ethyl acetate.

$^1$H-NMR (DMSO-$d_6$): 6.18-6.14 (m, 2 H); 6.14-6.09 (m, 2 H); 5.13 (br. s, 2 H); 4.32 (s, 4 H); 3.72 and 3.59 (d, J=14.5 Hz, 2 H); 3.55 and 3.52 (d, J=14.2 and 14.3 Hz, 2 H); 2.66-2.60 and 2.18-2.08 (m, 2 H); 2.02-1.93 and 1.68-1.50 (m, 4 H); 1.28-1.03 and 1.01-0.86 (m, 4 H).

$^{13}$C-NMR (DMSO-$d_6$): 154.15, 154.07, 154.05 and 153.88 (2 s); 107.28, 107.26, 106.86 and 106.57 (2 d); 59.97 and 54.69 (br.) (d); 55.60 (t); 42.92 and 42.79 (t); 30.45 and 27.15 (t); 24.46 and 21.87 (br.) (t).

Synthesis of (1RS,2SR)—N,N'-bis(pyridin-2-ylmethyl)cyclohexane-1,2-diamine

This compound was prepared as described in the general method (Method A) with pyridine-2-carboxaldehyde (1.88 g, 17.6 mmol) and (1RS,2SR)-1,2-diaminocyclohexane (1.00 g, 8.8 mmol) to give 2.33 g (90%) of the desired diamine.

$^1$H-NMR (DMSO-$d_6$): 8.52-8.46 (m, 2 H); 7.70 (dt, J=3.9, 1.8 Hz, 2 H); 7.42 (d, J=8.0 Hz, 2 H); 7.27-7.19 (m, 2 H); 3.76 (d, J=14.4 Hz, 2 H); 3.67 (d, J=14.4 Hz, 2 H); 2.71-2.63 (m, 2 H); 2.28 (br. s, 2 H); 1.81-1.45 (m, 4 H); 1.45-1.04 (m, 4 H).

$^{13}$C-NMR (DMSO-$d_6$): 160.67 (s); 148.65 (d); 136.25 (d); 121.98 (d); 121.71 (d); 55.77 (br. d); 51.98 (t); 30.74 and 27.44 (t); 22.00 (br. t).

Similarly, using the same procedure and product quantities, (cis/trans)-N,N'-bis(pyridin-2-ylmethyl)cyclohexane-1,2-diamine was prepared from (cis/trans)-1,2-diaminocyclohexane and pyridine-2-carboxaldehyde to give 2.12 g (82%) of the desired diamine.

$^1$H-NMR (DMSO-$d_6$): 8.51-8.45 (m, 2 H); 7.76-7.68 (m, 2 H); 7.50-7.39 (m, 2 H); 7.27-7.18 (m, 2 H); 3.89 and 3.76 (d, J=14.4 and 14.5 Hz, 2 H); 3.72 and 3.67 (d, J=14.5 and 14.3 Hz, 2 H); 2.70-2.64 and 2.27-2.17 (m, 2 H); 2.44 (br. s, 2 H); 2.07-1.96 and 1.74-1.48 (m, 4 H); 1.41-1.07 and 1.07-0.90 (m, 4 H).

$^{13}$C-NMR (DMSO-$d_6$): 160.92 and 160.62 (s); 148.61 and 148.54 (d); 136.22 (d); 121.94, 121.80, 121.67 and 121.63 (2 d); 60.54 and 55.71 (br.) (d); 51.93 and 51.72 (t); 30.74 and 27.40 (t); 24.46 and 21.96 (br.) (t).

Synthesis of N,N'-bis(furan-2-ylmethyl)propane-1,3-diamine

This compound was prepared as described in the general method (Method A) with furfural (2.59 g, 27.0 mmol), 1,3-diaminopropane (1.00 g, 13.5 mmol) and NaBH$_4$ (0.61 g, 16.1 mmol) to give 2.59 g (82%) of the desired diamine $^1$H-NMR (DMSO-$d_6$): 7.52 (dd, J=1.8, 1.0 Hz, 2 H); 6.36 (dd, J=3.2, 1.9 Hz, 2 H); 6.20 (dd, J=3.1, 0.8 Hz, 2 H); 3.63 (s, 4 H); 2.51 (t, J=6.9 Hz, 4 H); 1.98 (br. s, 2 H); 1.53 (quint., J=6.9 Hz, 2 H).

$^{13}$C-NMR (DMSO-$d_6$): 154.65 (s); 141.48 (d); 110.12 (d); 106.26 (d); 46.94 (t); 45.59 (t); 29.46 (t).

Synthesis of 1-(furan-2-yl)-N-(piperidin-2-ylmethyl)methanamine

This compound was prepared as described in the general method (Method A) with furfural (1.65 g, 17.2 mmol), 2-(aminomethyl)piperidine (2.00 g, 17.5 mmol) and NaBH$_4$ to give 1.87 g (55%) of the desired diamine $^1$H-NMR (CDCl$_3$): 7.34 (dd, J=1.8, 0.8 Hz, 1 H); 6.29 (dd, J=3.2, 1.9 Hz, 1 H); 6.15 (dd, J=3.1, 0.8 Hz, 1 H); 3.76 (s, 2 H); 3.08-3.03 (m, 1 H); 2.64-2.58 (m, 2 H); 2.58-2.50 (m, 1 H); 2.46 (dd, J=11.2, 8.7 Hz, 1 H); 1.81-1.74 (m, 1 H); 1.70 (br. s, 2 H); 1.62-1.50 (m, 2 H); 1.46-1.20 (m, 2 H); 1.13-1.03 (m, 1 H).

$^{13}$C-NMR (CDCl$_3$): 154.20 (s); 141.67 (d); 110.07 (d); 106.71 (d); 56.54 (d); 55.17 (t); 46.84 (t); 46.42 (t); 30.95 (t); 26.71 (t); 24.72 (t).

Synthesis of N-((1H-pyrrol-2-yl)methyl)-1-(piperidin-2-yl)methanamine

This compound was prepared as described in the general method (Method A) with pyrrole-2-carbaldehyde (1.67 g, 17.5 mmol) and 2-(aminomethyl)piperidine (2.00 g, 17.5 mmol) to give 1.85 g (55%) of the desired diamine.

$^1$H-NMR (DMSO-$d_6$): 10.56 (br. s, 1 H); 6.62-6.57 (m, 1 H); 5.92-5.85 (m, 1 H); 5.85-5.80 (m, 1 H); 3.58 (dd, J=18.5, 13.6 Hz, 2 H); 2.95-2.87 (m, 1 H); 2.52-2.38 (m, 4 H); 2.31 (dd, J=12.3, 9.2 Hz, 1 H); 1.76-1.63 (m, 1 H); 1.52-1.41 (m, 2 H); 1.34-1.20 (m, 2 H); 1.02-0.87 (m, 1 H).

$^{13}$C-NMR (DMSO-$d_6$): 130.91 (s); 116.39 (d); 106.74 (d); 105.33 (d); 56.03 (d); 54.75 (t); 46.25 (t); 46.09 (t); 30.58 (t); 26.27 (t); 24.49 (t).

Synthesis of 1-(piperidin-2-yl)-N-(thiophen-2-ylmethyl)methanamine

This compound was prepared as described in the general method (Method A) with thiophene-2-carbaldehyde (1.96 g, 17.5 mmol), 2-(aminomethyl)piperidine (2.06 g, 17.5 mmol) and NaBH$_4$ (0.65 g, 17.2 mmol) to give 1.72 g (45%) of the desired diamine $^1$H-NMR (CDCl$_3$): 7.18 (dd, J=5.1, 1.3 Hz, 1 H); 6.93 (dd, J=5.1, 3.3 Hz, 1 H); 6.91-6.88 (m, 1 H); 3.97 (dd, J=2.0, 0.8 Hz, 2 H); 3.10-3.03 (m, 1 H); 2.70-2.46 (m, 4 H); 1.82-1.73 (m, 1 H); 1.66 (br. s, 2 H); 1.63-1.52 (m, 2 H); 1.47-1.25 (m, 2 H); 1.16-1.03 (m, 1 H).

$^{13}$C-NMR (CDCl$_3$): 144.57 (s); 126.55 (d); 124.64 (d); 124.24 (d); 56.56 (d); 55.20 (t); 48.63 (t); 46.86 (t); 30.95 (t); 26.72 (t); 24.73 (t).

Synthesis of N-((1H-pyrrol-2-yl)methyl)cyclohexanamine

This compound was prepared as described in the general method (Method A) with pyrrole-2-carbaldehyde (1.92 g, 20.2 mmol), aminocyclohexane (2.00 g, 20.2 mmol) and NaBH$_4$ (0.46 g, 12.2 mmol) to give 0.48 g (13%) of the desired diamine $^1$H-NMR (DMSO-$d_6$): 10.52 (br. s, 1 H); 6.61-6.56 (m, 1 H); 5.90-5.85 (m, 1 H); 5.84-5.79 (m, 1 H); 3.63 (s, 2 H); 2.39-2.29 (m, 1 H); 1.84-1.75 (m, 2 H); 1.70-1.60 (m, 3 H); 1.57-1.48 (m, 1 H); 1.25-1.07 (m, 3 H); 1.07-0.90 (m, 2 H).

$^{13}$C-NMR (DMSO-$d_6$): 131.15 (s); 116.34 (d); 106.74 (d); 105.20 (d); 54.93 (d); 42.97 (t); 32.76 (t); 25.88 (t); 24.37 (t).

Synthesis of (cis/trans)-N,N'-bis(furan-2-ylmethyl)cyclohexane-1,3-diamine

This compound was prepared as described in the general method (Method A) with furfural (1.68 g, 17.5 mmol) and (cis/trans)-1,3-diaminocyclohexane (1.00 g, 8.8 mmol) to give 1.87 g (78%) of the desired diamine (ratio cis/trans ca. 2.5:1).

$^1$H-NMR (DMSO-$d_6$, cis): 7.52 (dd, J=1.8, 0.8 Hz, 2 H); 6.36 (dd, J=3.1, 1.9 Hz, 2 H); 6.23-6.18 (m, 2 H); 3.69 (s, 4 H); 2.33 (tt, J=11.0, 3.6 Hz, 2 H); 2.26-1.87 (br. s and m, 3 H); 1.86-1.75 (m, 2 H); 1.70-1.60 (m, 1 H); 1.12 (qt, J=13.2, 3.4, 1 H); 0.94-0.82 (m, 1 H); 0.78 (q, J=11.5, 2 H).

$^1$H-NMR (DMSO-$d_6$, trans): 7.52 (dd, J=1.8, 0.8 Hz, 2 H); 6.36 (dd, J=3.1, 1.9 Hz, 2 H); 6.23-6.18 (m, 2 H); 3.65 (s, 4 H); 2.83-2.75 (m, 2 H); 2.26-1.87 (br. s, 2 H); 1.58-1.42 (m, 6 H); 1.31-1.20 (m, 2 H).

$^{13}$C-NMR (DMSO-$d_6$, cis): 154.84 (s); 141.43 (d); 110.13 (d); 106.15 (d); 54.39 (d); 42.68 (t); 39.70 (t); 32.46 (t); 22.51 (t).

$^{13}$C-NMR (DMSO-$d_6$, trans): 154.88 (s); 141.43 (d); 110.13 (d); 106.18 (d); 50.50 (d); 42.88 (t); 36.87 (t); 31.25 (t); 19.16 (t).

Synthesis of (cis/trans)-N,N'-bis((1H-pyrrol-2-yl)methyl)cyclohexane-1,3-diamine This compound was prepared as described in the general method (Method A) with pyrrole-2-carboxaldehyde (1.67 g, 17.5 mmol) and (cis/trans)-1,3-diaminocyclohexane (1.00 g, 8.8 mmol) to give 1.62 g (68%) of the desired diamine (ratio cis/trans ca. 2.5:1).

$^1$H-NMR (DMSO-$d_6$, cis): 10.52 (br. s, 2 H); 6.62-6.55 (m, 2 H); 5.92-5.85 (m, 2 H); 5.85-5.79 (m, 2 H); 3.63 (s, 4 H); 2.40-2.27 (m, 2 H); 2.11-2.02 (m, 1 H); 1.87-1.73 (m, 2 H); 1.72-1.58 (m, 1 H); 1.20-1.03 (m, 1 H); 0.96-0.81 (m, 1 H); 0.78 (q, J=11.4, 2 H).

$^1$H-NMR (DMSO-$d_6$, trans): 10.52 (br. s, 2 H); 6.62-6.55 (m, 2 H); 5.92-5.85 (m, 2 H); 5.85-5.79 (m, 2 H); 3.59 (m, 4 H); 2.84-2.75 (m, 2 H); 1.58-1.40 (m, 6 H); 1.32-1.20 (m, 2 H).

$^{13}$C-NMR (DMSO-$d_6$, cis): 131.03 (s); 116.35 (d); 106.74 (d); 105.24 (d); 54.33 (d); 43.01 (t); 39.93 (t); 32.58 (t); 22.59 (t).

$^{13}$C-NMR (DMSO-$d_6$, trans): 131.11 (s); 116.35 (d); 106.74 (d); 105.24 (d); 50.46 (d); 43.22 (t); 37.16 (t); 31.33 (t); 19.20 (t).

Synthesis of (cis/trans)-N,N'-bis(pyridin-2-ylmethyl)cyclohexane-1,3-diamine

This compound was prepared as described in the general method (Method A) with pyridine-2-carboxaldehyde (1.88 g, 17.5 mmol) and (cis/trans)-1,3-diaminocyclohexane (1.00 g, 8.8 mmol) to give 1.65 g (64%) of the desired diamine (ratio cis/trans ca. 2.5:1).

$^1$H-NMR (DMSO-$d_6$, cis): 8.50-8.46 (m, 2 H); 7.76-7.68 (m, 2 H); 7.50-7.39 (m, 2 H); 7.26-7.18 (m, 2 H); 3.82 (s, 4 H); 2.42-2.32 (m, 2 H); 2.19-2.10 (m, 1 H); 1.90-1.80 (m, 2 H); 1.71-1.62 (m, 1 H); 1.17-1.06 (m, 1 H); 1.01-0.83 (m, 3 H).

$^1$H-NMR (DMSO-$d_6$, trans): 8.50-8.46 (m, 2 H); 7.76-7.68 (m, 2 H); 7.50-7.39 (m, 2 H); 7.26-7.18 (m, 2 H); 3.78 (m, 4 H); 2.89-2.80 (m, 2 H); 1.62-1.47 (m, 6 H); 1.37-1.26 (m, 2 H).

$^{13}$C-NMR (DMSO-$d_6$, cis): 160.81 (s); 148.53 (d); 136.22 (d); 121.73 (d); 121.60 (d); 54.99 (d); 51.74 (t); 40.29 (t); 32.75 (t); 22.54 (t).

$^{13}$C-NMR (DMSO-$d_6$, trans): 160.79 (s); 148.53 (d); 136.20 (d); 121.79 (d); 121.60 (d); 51.97 (d); 51.11 (d); 37.35 (t); 31.52 (t); 19.25 (t).

Synthesis of N,N'-bis(furan-2-ylmethyl)ethane-1,2-diamine

This compound was prepared as described in the general method (Method B) with 1,2-diaminoethane (1.00 g, 16.6 mmol), furfural (3.20 g, 33.3 mmol) and NaBH$_4$ (1.76 g, 46.6 mmol) to give 3.51 g (96%) of the desired diamine.

$^1$H-NMR (CDCl$_3$): 7.34 (dd, J=2.1, 0.8 Hz, 2 H); 6.29 (dd, J=3.1, 1.8 Hz, 2 H); 6.17-6.13 (m, 2 H); 3.76 (s, 4 H); 2.72 (s, 4 H); 1.65 (br. s, 2 H).

$^{13}$C-NMR (CDCl$_3$): 154.06 (s); 141.71 (d); 110.07 (d); 106.77 (d); 48.38 (t); 46.10 (t).

Synthesis of N,N'-bis(pyridin-2-ylmethyl)ethane-1,2-diamine

This compound was prepared as described in the general method (Method B) with 1,2-diaminoethane (0.28 g, 4.7 mmol), 2-pyridinecarboxaldehyde (1.05 g, 9.8 mmol) and NaBH$_4$ (0.49 g, 13.1 mmol) to give 0.99 g (88%) of the desired diamine.

$^1$H-NMR (CDCl$_3$): 8.57-8.52 (m, 2 H); 7.62 (dt, J=7.6, 1.9 Hz, 2 H); 7.34-7.29 (m, 2 H); 7.17-7.11 (m, 2 H); 3.92 (s, 4 H); 2.82 (s, 4 H); 2.13 (br. s, 2 H).

$^{13}$C-NMR (CDCl$_3$): 160.02 (s); 149.25 (d); 136.36 (d); 122.19 (d); 121.83 (d); 55.23 (t); 49.13 (t).

Synthesis of N,N'-bis(furan-2-ylmethyl)propane-1,2-diamine

This compound was prepared as described in the general method (Method A) with 1,2-diaminopropane (1.00 g, 13.5 mmol), furfural (2.20 g, 22.9 mmol) and NaBH$_4$ (0.52 g, 13.7 mmol) to give 1.90 g of the crude diamine Plug filtration (SiO$_2$, ethyl acetate/ethanol 95:5) of 0.50 g afforded 0.20 g (24%) of the pure product.

$^1$H-NMR (CDCl$_3$): 7.37-7.31 (m, 2 H); 6.33-6.27 (m, 2 H); 6.18-6.12 (m, 2 H); 3.83 (d, J=14.3 Hz, 1 H); 3.73 (s, 2 H); 3.71 (d, J=13.6 Hz, 1 H); 2.77-2.68 (m, 1 H); 2.61 (dd, J=11.8, 4.1 Hz, 1 H); 2.46 (dd, J=11.8, 8.5 Hz, 1 H); 1.73 (br. s, 2 H); 1.03 (d, J=6.2 Hz, 3 H).

$^{13}$C-NMR (CDCl$_3$): 154.35 (s); 154.22 (s); 141.67 (d); 141.64 (d); 110.07 (d, 2C); 106.72 (d); 106.59 (d); 54.67 (t); 51.49 (d); 46.09 (t); 43.76 (t); 18.47 (q).

Use of active aldehydes or ketones

The following examples illustrate the formation of dynamic mixtures using perfuming ingredients as active aldehydes or ketones. However, they are also representative for the generation of dynamic mixtures according to the present invention in which the active aldehydes or ketones are useful as insect repellents or attractants and can be used also as malodor counteracting. Some of the compounds described in the following examples, such as benzaldehyde, decanal, 2,4-dimethyl-3-cyclohexene-1-carbaldehyde, 3,7-dimethyl-6-octenal (citronellal), 2-furancarbaldehyde (furfural), 2-heptanone, 1,8-p-menthadien-7-al, 1-(4-methylphenyl)-1-ethanone (4-methylacetophenone) or 10-undecenal, are also known to be insect attractants or repellents (see for example: A. M. El-Sayed, The Pherobase 2005, http://www.pherobase.net).

Example 1

Performance of a softener base comprising an invention's dynamic mixture

The use as perfuming ingredient of the present invention's mixture has been tested in a fabric softener. A fabric softener base with the following final composition has been prepared:

| | |
|---|---|
| Stepantex ® VL90 A (origin: Stepan) | 16.5% by weight |
| Calcium chloride (10% aq. solution) | 0.6% by weight |
| Water | 82.9% by weight |

An equimolar mixture (0.041 M) of the following aldehydes and ketones was obtained by weighing them into a 100 mL flask and filling up with ethanol: furfural (394.0 mg), Trifernal® (607.6 mg), Delphone (632.4 mg), 10-undecenal (690.0 mg), Vertral® (673.6 mg), 2-heptanone (468.0 mg), benzaldehyde (453.2 mg), Triplal® (566.8 mg), 4-ethylbenzaldehyde (550.0 mg), 1-(4-methylphenyl)-1-ethanone (4-methylacetophenone, 550.0 mg), decanal (607.6 mg), methoxymelonal (706.4 mg), 1,8-p-menthadien-7-al (615.2 mg), 2-methyldecanal (698.0 mg), Liminal® (681.6 mg), 3,5,5-trimethylhexanal (583.2 mg), 2,4,6-trimethyl-3-cyclohexene-1-carbaldehyde (624.0 mg) and benzylacetone (607.6 mg). The samples were prepared by adding one of the diamines (0.369 mmol=18×0.0205 mmol) to 1.80 g of the above fabric softener base into a small vial. To another vial, serving as the reference, 1.80 g of the above fabric softener base were added. Then 0.5 mL of the solution containing equimolar amounts (0.0205 mmol) of the fragrance aldehydes and/or ketones and 1.5 mL of ethanol were added to both vials. The two samples were closed and left standing at room temperature to equilibrate. After 5 days, the samples were dispersed in a beaker with 600 mL of demineralized cold tap water, respectively. One cotton towel (cut to ca. 12×12 cm sheets) was added to each beaker and agitated manually for 3 min, left standing for 2 min, then wrung out by hand and weighed to obtain a constant quantity of residual water. The two towels were left drying overnight and analyzed the next day.

Each towel was put into a headspace sampling cell (160 mL) thermostated at 25° C. and exposed to a constant air flow of ca. 200 mL/min. The air was filtered through active charcoal and aspirated through a saturated solution of NaCl (to ensure a constant humidity of the air of ca. 75%). During 135 min the headspace system was left equilibrating, then the volatiles were adsorbed during 15 minutes on a clean Tenax® cartridge. The cartridges were desorbed on a Perkin Elmer TurboMatrix ATD 350 desorber coupled to a Perkin Elmer Autosystem XL gas chromatograph equipped with a J&W Scientific DB1 capillary column (30 m, i.d. 0.32 mm, film 1.50 μm) and a Perkin Elmer Turbomass Upgrade mass spectrometer. The volatiles were analyzed by gas chromatography (GC) using a two step temperature gradient starting at 90° C. for 10 min, then going to 135° C. at 2° C./min. Headspace concentrations (in ng/L air) were obtained by external standard calibrations of the corresponding fragrance aldehydes and ketones using ethanol solutions of five different concentrations. 0.1, 0.2 or 0.3 μl of the calibration solutions were injected onto Tenax® cartridges, which were immediately desorbed under the same conditions as those resulting from the headspace sampling.

To determine the distribution of the improved aldehyde performance, we measured a "perfumery ingredient's intensity variation" ($\Delta I_{mix}$) for a given mixture of aldehydes and ketones by comparing the intensity of the individual perfumery ingredients in the presence of different diamine derivatives with their intensities without diamine derivative (reference). For each individual aldehyde or ketone i in the mixture, an individual intensity ratio $I_i$ was determined as follows:

$$I_i = \frac{[c_i]_d}{[c_i]_r} \quad \text{(Eq. 1)}$$

wherein $[c_i]_d$ is the measured headspace concentration of aldehyde or ketone i in the mixture in the presence of the diamine derivative and $[c_i]_r$ the measured headspace concentration of aldehyde or ketone i in the mixture in the absence of the diamine derivative (reference). The total intensity ratio of the mixture $I_{mix}$ was then obtained as the average value of the individual intensity ratios $I_i$ as follows:

$$I_{mix} = \frac{\sum I_i}{n_t} \quad \text{(Eq. 2)}$$

wherein $n_t$ is the total number of aldehydes and ketones present in the mixture, in the present example $n_t$ is 18. The perfumery ingredient's intensity variation $\Delta I_{mix}$ is the standard deviation of this average value $I_{mix}$. $\Delta I_{mix}$ gives an indication on the uniformity of distribution (variation). The final values were rounded to an integer number. A more evenly distributed aldehyde/ketone performance is expressed by a lower $\Delta I_{mix}$ value. For the reference composition the $\Delta I_{mix}$ value is by definition equal to 1. A $\Delta I_{mix}$ value below 1, indicates that headspace concentrations of the majority of the perfuming compounds are in fact decreased as compared to the reference, and therefore the problem of the invention is not solved since the performance of the perfuming ingredients in the mixture decreased (this is the case for the diamines described in WO 2010/142480). Therefore, in order to solve the above-mentioned problems, the invention's delivery system should ideally give rise to higher headspace concentrations for almost all the perfuming aldehydes and/or ketones in the mixture and thus give a $\Delta I_{mix}$ value as close as possible to 1. To show an improvement over the prior art diamine derivatives, the invention's $\Delta I_{mix}$ value should be comprised between the ones of the prior art diamine derivatives and 1, possibly as close as possible to 1. Any $\Delta I_{mix}$ value below 1 indicates that the system is performing less than the free perfume and therefore has a negative impact. As the following tables show, the invention's problems are solved by the present invention.

The following headspace concentrations were measured on dry fabric in the absence (reference) or in the presence of one of the diamines A-X. All data are average values of at least two measurements, values were rounded. The results are reported in the following tables.

TABLE 1

Results for various cyclohexane-1,2-diamine derivatives (prior art (*) B vs present invention C-I)

Headspace concentrations for a mixture of aldehydes and ketones [ng/L] on dry fabric (1 day after washing)

|  | Reference | A* | B* | C | D |
|---|---|---|---|---|---|
| Furfural | 12.1 | 0.1 | 197.4 | 917.8 | 2560.4 |
| 2-Heptanone | 0.5 | 0.4 | 0.4 | 0.9 | 0.6 |
| Benzaldehyde | 9.9 | 14.9 | 1115.5 | 292.3 | 764.5 |
| 3,5,5-Trimethylhexanal | 2.5 | 3.6 | 960.0 | 678.5 | 387.6 |
| Triplal ® | 35.1 | 0.3 | 88.0 | 8.2 | 14.7 |
| 2,4,6-Trimethyl-3-cyclo-hexene-1-carbaldehyde | 0.1 | 0.1 | 1.1 | 1.4 | 3.1 |
| 4-Ethylbenzaldehyde | 10.0 | 0.2 | 206.8 | 231.1 | 740.5 |
| 4-Methylacetophenone | 0.6 | 0.1 | 0.2 | 24.2 | 0.1 |
| Trifernal ® | 9.9 | 0.8 | 109.1 | 136.6 | 262.3 |
| Decanal | 46.0 | 35.6 | 128.2 | 261.5 | 333.8 |
| Methoxymelonal | 6.2 | 0.8 | 137.7 | 86.6 | 122.7 |
| Benzylacetone | 1.3 | 0.2 | 0.2 | 40.6 | 1.5 |
| Delphone | 1.1 | 0.1 | 0.2 | 3.1 | 0.1 |
| 1,8-p-Menthadien-7-al | 5.9 | 1.5 | 178.5 | 82.4 | 408.7 |
| 2-Methyldecanal | 25.4 | 5.3 | 199.9 | 327.6 | 634.4 |
| 10-Undecenal | 25.0 | 2.6 | 43.3 | 146.9 | 255.1 |
| Liminal ® | 9.8 | 1.5 | 185.6 | 286.0 | 441.9 |
| Vertral ® | 6.4 | 3.4 | 381.3 | 197.1 | 239.3 |
| $\Delta I_{mix}$ | 1 | 0.5 | 92 | 63 | 58 |

|  | E | F | G | H | I |
|---|---|---|---|---|---|
| Furfural | 644.3 | 87.6 | 172.9 | 33.2 | 15.0 |
| 2-Heptanone | 1.6 | 0.2 | 1.1 | 0.9 | 2.5 |
| Benzaldehyde | 50.0 | 148.5 | 351.0 | 251.8 | 102.1 |
| 3,5,5-Trimethylhexanal | 60.1 | 272.8 | 34.2 | 8.9 | 11.6 |
| Triplal ® | 6.7 | 4.8 | 4.6 | 2.8 | 2.5 |
| 2,4,6-Trimethyl-3-cyclo-hexene-1-carbaldehyde | 3.2 | 1.8 | 1.8 | 0.3 | 0.5 |
| 4-Ethylbenzaldehyde | 146.7 | 162.5 | 209.1 | 253.6 | 98.0 |
| 4-Methylacetophenone | 0.4 | 13.9 | 0.4 | 46.1 | 32.9 |
| Trifernal ® | 217.0 | 97.0 | 30.8 | 29.7 | 20.7 |
| Decanal | 274.4 | 119.1 | 126.0 | 96.3 | 77.2 |
| Methoxymelonal | 70.6 | 78.5 | 17.5 | 33.4 | 22.7 |
| Benzylacetone | 4.6 | 28.6 | 1.0 | 74.5 | 42.6 |
| Delphone | 0.3 | 1.6 | 0.1 | 4.1 | 2.6 |
| 1,8-p-Menthadien-7-al | 42.1 | 57.0 | 35.6 | 95.5 | 24.6 |
| 2-Methyldecanal | 172.5 | 189.9 | 114.0 | 232.8 | 138.9 |
| 10-Undecenal | 424.0 | 74.1 | 117.6 | 89.1 | 63.8 |

TABLE 1-continued

Results for various cyclohexane-1,2-diamine derivatives (prior art (*) B vs present invention C-I)

Headspace concentrations for a mixture of aldehydes and ketones [ng/L] on dry fabric (1 day after washing)

| | | | | | |
|---|---|---|---|---|---|
| Liminal ® | 325.9 | 142.6 | 40.2 | 62.2 | 37.4 |
| Vertral ® | 89.2 | 114.8 | 12.7 | 45.8 | 29.1 |
| $\Delta I_{mix}$ | 14 | 25 | 9 | 20 | 13 |

Reference compounds described in the prior art are marked with an asterisk (*).
A = N,N'-dimethylethane-1,2-diamine, reported in DE 10-2005-062175 and in WO 2010/142480;
B = (cis/trans)-N,N'-dibenzylcyclohexane-1,2-diamine, reported in WO 08/093272;
C = (cis/trans)-N,N'-bis(2-furanylmethyl)cyclohexane-1,2-diamine;
D = (cis)-N,N'-bis(2-furanylmethyl)cyclohexane-1,2-diamine.
E = (trans)-N,N'-bis(2-furanylmethyl)cyclohexane-1,2-diamine;
F = (cis/trans)-N,N'-bis((5-methylfuran-2-yl)methyl)cyclohexane-1,2-diamine;
G = (cis/trans)-(5,5'-((cyclohexane-1,2-diylbis(azanediyl))bis(methylene))bis(furan-5,2-diyl))dimethanol;
H = (cis)-N,N'-bis(pyridin-2-ylmethyl)cyclohexane-1,2-diamine;
I = (cis/trans)-N,N'-bis(pyridin-2-ylmethyl)cyclohexane-1,2-diamine.

TABLE 2

Results for various propane-1,3-diamine derivatives (prior art (*) J vs. present invention K), or for various (piperidin-2-ylmethyl)-methanamine derivatives (prior art (*) L vs. present invention M-O) (to be compared with values of the reference of Table 1)

Headspace concentrations for a mixture of aldehydes and ketones [ng/L] on dry fabric (1 day after washing)

| | J* | K | L* | M | N | O |
|---|---|---|---|---|---|---|
| Furfural | 201.0 | 75.8 | 119.2 | 598.4 | 9.0 | 282.4 |
| 2-Heptanone | 0.2 | 3.1 | 0.9 | 1.3 | 0.5 | 0.4 |
| Benzaldehyde | 1133.5 | 137.5 | 1226.6 | 677.5 | 51.8 | 657.0 |
| 3,5,5-Trimethylhexanal | 6.5 | 248.0 | 150.8 | 118.7 | 30.1 | 146.1 |
| Triplal ® | 0.4 | 6.8 | 66.1 | 252.2 | 12.9 | 129.6 |
| 2,4,6-Trimethyl-3-cyclo-hexene-1-carbaldehyde | 0.2 | 4.9 | 1.1 | 0.9 | 1.4 | 0.9 |
| 4-Ethylbenzaldehyde | 505.6 | 143.6 | 499.8 | 683.7 | 81.8 | 531.1 |
| 4-Methylacetophenone | 0.1 | 35.6 | 1.0 | 1.5 | 31.4 | 0.1 |
| Trifernal ® | 76.5 | 83.2 | 94.8 | 103.7 | 46.5 | 114.4 |
| Decanal | 77.4 | 107.9 | 289.4 | 272.5 | 98.0 | 280.5 |
| Methoxymelonal | 0.2 | 75.4 | 92.7 | 58.6 | 45.1 | 141.9 |
| Benzylacetone | 0.0 | 48.1 | 1.3 | 1.3 | 43.4 | 0.1 |
| Delphone | 0.1 | 4.4 | 0.5 | 0.4 | 1.2 | 0.2 |
| 1,8-p-Menthadien-7-al | 372.7 | 62.2 | 304.0 | 283.2 | 21.1 | 313.2 |
| 2-Methyldecanal | 4.7 | 191.6 | 776.6 | 251.1 | 84.3 | 799.3 |
| 10-Undecenal | 70.5 | 64.8 | 202.4 | 266.5 | 109.7 | 240.4 |
| Liminal ® | 87.9 | 128.9 | 265.7 | 162.7 | 64.9 | 264.4 |
| Vertral ® | 2.3 | 107.7 | 108.8 | 100.6 | 74.6 | 104.6 |
| $\Delta I_{mix}$ | 31 | 25 | 31 | 24 | 13 | 22 |

Reference compounds described in the prior art are marked with an asterisk (*).
J = N,N'-dibenzylpropane-1,3-diamine, reported in WO 08/093272;
K = N,N'-bis(2-furanylmethyl)propane-1,3-diamine;
L = 1-benzyl-N-(piperidin-2-ylmethyl)methanamine, reported in WO 08/093272;
M = 1-(furan-2-yl)-N-(piperidin-2-ylmethyl)methanamine;
N = N-((1H-pyrrol-2-yl)methyl)-1-(piperidin-2-yl)methanamine;
O = 1-(piperidin-2-yl)-N-(thiophen-2-ylmethyl)methanamine.

TABLE 3

Results for various cyclohexane-1,3-diamine derivatives (prior art (*) P vs. present invention R-S) (reference values taken from Table 1)

Headspace concentrations for a mixture of aldehydes and ketones [ng/L] on dry fabric (1 day after washing)

| | Reference | P* | Q | R | S |
|---|---|---|---|---|---|
| Furfural | 12.1 | 48.5 | 151.4 | 10.6 | 14.0 |
| 2-Heptanone | 0.5 | 1.0 | 0.2 | 0.2 | 0.6 |
| Benzaldehyde | 9.9 | 519.4 | 9.6 | 19.5 | 15.2 |
| 3,5,5-Trimethylhexanal | 2.5 | 25.2 | 6.1 | 57.5 | 5.7 |
| Triplal ® | 35.1 | 72.4 | 3.4 | 5.5 | 3.9 |
| 2,4,6-Trimethyl-3-cyclo-hexene-1-carbaldehyde | 0.1 | 5.9 | 0.0 | 1.8 | 0.3 |
| 4-Ethylbenzaldehyde | 10.0 | 61.0 | 5.8 | 27.6 | 13.8 |
| 4-Methylacetophenone | 0.6 | 0.7 | 0.9 | 19.6 | 19.8 |
| Trifernal ® | 9.9 | 28.2 | 11.3 | 55.6 | 19.4 |
| Decanal | 46.0 | 131.7 | 43.6 | 83.7 | 74.2 |
| Methoxymelonal | 6.2 | 21.2 | 10.2 | 36.9 | 23.1 |
| Benzylacetone | 1.3 | 1.1 | 1.4 | 36.0 | 28.2 |
| Delphone | 1.1 | 4.1 | 0.2 | 0.9 | 1.2 |
| 1,8-p-Menthadien-7-al | 5.9 | 22.4 | 2.6 | 20.1 | 5.2 |
| 2-Methyldecanal | 25.4 | 131.4 | 25.1 | 78.6 | 30.8 |
| 10-Undecenal | 25.0 | 55.8 | 29.9 | 74.9 | 64.6 |
| Liminal ® | 9.8 | 61.3 | 11.5 | 89.2 | 23.0 |

TABLE 3-continued

Results for various cyclohexane-1,3-diamine derivatives (prior art (*) P vs. present invention R-S) (reference values taken from Table 1)

| | Headspace concentrations for a mixture of aldehydes and ketones [ng/L] on dry fabric (1 day after washing) | | | | |
|---|---|---|---|---|---|
| | Reference | P* | Q | R | S |
| Vertral ® | 6.4 | 23.0 | 5.9 | 76.0 | 17.3 |
| $\Delta I_{mix}$ | 1 | 14 | 3 | 10 | 8 |

P = N,N'-dibenzylcyclohexane-1,3-diamine, reported in WO 08/093272;
Q = N,N'-bis(furan-2-ylmethyl)cyclohexane-1,3-diamine;
R = N,N'-bis((1H-pyrrol-2-yl)methyl)cyclohexane-1,3-diamine;
S = N,N'-bis(pyridin-2-ylmethyl)cyclohexane-1,3-diamine.

TABLE 4

Results for various ethane-1,2-diamine derivatives (prior art (*) T vs. present invention U-W) and for the invention's 1H-pyrrol derivative (X) (reference values taken from Table 1)

| | Headspace concentrations for a mixture of aldehydes and ketones [ng/L] on dry fabric (1 day after washing) | | | | |
|---|---|---|---|---|---|
| | Reference | T* | U | V | W | X |
| Furfural | 12.1 | 0.1 | 441.1 | 31.1 | 101.0 | 7.6 |
| 2-Heptanone | 0.5 | 0.4 | 1.1 | 0.8 | 0.1 | 1.4 |
| Benzaldehyde | 9.9 | 721.0 | 207.0 | 48.8 | 78.6 | 8.7 |
| 3,5,5-Trimethylhexanal | 2.5 | 2.3 | 23.9 | 12.4 | 13.9 | 32.5 |
| Triplal ® | 35.1 | 2.7 | 113.6 | 67.5 | 9.7 | 7.9 |
| 2,4,6-Trimethyl-3-cyclo-hexene-1-carbaldehyde | 0.1 | 3.0 | 0.4 | 0.1 | 4.2 | 0.1 |
| 4-Ethylbenzaldehyde | 10.0 | 218.9 | 289.3 | 36.4 | 54.1 | 5.1 |
| 4-Methylacetophenone | 0.6 | 0.1 | 1.1 | 0.5 | 0.1 | 0.0 |
| Trifernal ® | 9.9 | 19.1 | 95.3 | 10.2 | 42.5 | 43.8 |
| Decanal | 46.0 | 90.1 | 128.4 | 60.5 | 30.3 | 65.1 |
| Methoxymelonal | 6.2 | 2.7 | 25.9 | 11.5 | 9.6 | 17.6 |
| Benzylacetone | 1.3 | 0.0 | 0.3 | 0.8 | 0.1 | 1.4 |
| Delphone | 1.1 | 0.0 | 6.8 | 4.3 | 0.7 | 0.2 |
| 1,8-p-Menthadien-7-al | 5.9 | 389.9 | 202.7 | 10.6 | 81.5 | 6.4 |
| 2-Methyldecanal | 25.4 | 44.6 | 100.4 | 17.7 | 40.3 | 46.7 |
| 10-Undecenal | 25.0 | 58.2 | 123.4 | 17.7 | 33.1 | 62.4 |
| Liminal ® | 9.8 | 28.2 | 90.6 | 17.9 | 33.8 | 53.5 |
| Vertral ® | 6.4 | 3.4 | 38.9 | 21.4 | 16.9 | 45.5 |
| $\Delta I_{mix}$ | 1 | 22 | 12 | 1.5 | 7 | 3 |

T = N,N'-dibenzylethane-1,2-diamine, reported in WO 08/093272;
U = N,N'-bis(furan-2-ylmethyl)ethane-1,2-diamine;
V = N,N'-bis(pyridin-2-ylmethyl)ethane-1,2-diamine;
W = N,N'-bis(furan-2-ylmethyl)propane-1,2-diamine;
X = N-((1H-pyrrol-2-yl)methyl)cyclohexanamine.

The data show that the presence of a diamine derivative according to the present invention increases the headspace concentrations of the volatile aldehydes (and to a lower extent of the ketones) from the mixture with respect to the reference without diamine. The structure of the diamine derivative and the nature of the substituent at the N-atom of the diamine are very important for the performance of the dynamic mixture. The presence of prior art diamine N,N'-dimethylethane-1,2-diamine (A) in the mixture only marginally increased the headspace concentration of the volatiles (the headspace concentrations remained below 15 ng/L, with the exception of aliphatic, linear aldehyde decanal where a headspace concentration of 35.6 ng/L was measured). The overall performance of prior art diamine A is thus insufficient for practical applications. Considerably higher headspace concentrations (in some cases even above 1000 ng/L) were obtained in the presence of the diamines according to the present invention, allowing practical applications. Such higher headspace concentrations were also observed for the diamine derivatives described in WO 08/093272.

When the performance of the diamine derivatives according to the invention are compared to the ones of the derivatives described in WO 08/093,272, the diamine derivatives of the present invention have the particular advantage to give a more evenly distributed effect of improved performance with respect to the systems described in WO 08/093,272. Thus the present invention has the advantage of minimizing odor distortions obtainable when only a few perfuming ingredients are boosted in the headspace. This is demonstrated by the comparison of the perfumery ingredient's intensity variation ($\Delta I_{mix}$) in the presence of different diamine derivatives as compared to the reference without diamine derivative. Cyclohexane-1,2-diamines (C-I) according to the present invention all display lower $\Delta I_{mix}$ values and thus a more evenly distributed aldehyde/ketone performance than the structurally related prior art compound (B). With a $\Delta I_{mix}$ of 92 prior art diamine B displays the highest values of this series. Similarly, lower perfumery ingredient's intensity variation values were measured for the diamine derivatives of the present invention as compared to prior art diamines, as shown for the series of 1,3-propanediamines (J vs. K), N-(piperidin-2-ylmethyl) methanamines (L vs. M-O), cyclohexane-1,3-diamines (P vs. Q-S) and 1,2-ethanediamine derivatives (T vs. U-W).

Therefore, the use of diamine derivatives according to the present invention not only improves the performance of volatile aldehydes (and ketones) in practical applications by the in situ formation of dynamic mixtures, but it also gives rise to a more even distribution of this improvement over the compounds in the mixture than in the systems described in the prior art (see FIGS. 1 and 2).

Example 2

Performance of an all purpose cleaner base comprising an invention's dynamic mixture The use as perfuming ingredient of the present invention's mixture has been tested in an all purpose cleaner (APC). An APC base with the following final composition has been prepared:

| | |
|---|---|
| Neodol ® 91-8 (origin: Shell Chemicals) | 5.0% by weight |
| Marlon ® A 375 (origin: Hüls AG) | 4.0% by weight |
| Sodium cumolsulphonate | 2.0% by weight |
| Kathon ® CG (origin: Rohm and Haas) | 0.2% by weight |
| Water | 88.8% by weight |

An equimolar mixture (0.041 M) of aldehydes and ketones was obtained as described in Example 1 by weighing the compounds into a 100 mL flask and filling up with ethanol. This solution was then diluted by a factor of 2.5 to obtain a diluted mixture. The samples were prepared by adding 0.5 mL of the diluted mixture of aldehydes and ketones, 1.5 mL of ethanol and 10 mL of the above described APC base to the diamine (0.148 mmol=18×0.0082 mmol). Another sample, serving as the reference, was prepared in the same way without adding a diamine. The samples were shaken vigorously and left standing in a closed flask at room temperature to equilibrate. After 5 days, the samples were diluted to 10% (by adding 9 mL of demineralized tap water to 1 mL of the sample). The samples were then deposited as a film onto a glass plate (ca. 4×13 cm) and a porous ceramic plate (ca. 5×10 cm) by carefully pipetting 0.75 mL of the mixture onto the surface of the respective substrate. The samples were then pairwise covered with a 2 or 4 L crystallizing dish and left standing at room temperature. After one day, the substrates were each placed into a headspace sampling cell (ca. 625 mL) and exposed to a constant air flow of ca. 200 ml/min. The air was filtered through active charcoal and aspirated through a saturated solution of NaCl (to ensure a constant humidity of the air of ca. 75%). During 135 min the headspace system was left equilibrating, and then the volatiles were adsorbed during 15 minutes on a clean Tenax® cartridge. The cartridges were desorbed on a Perkin Elmer TurboMatrix ATD 350 desorber coupled to an Agilent 7890A gas chromatograph equipped with a HP 5MS capillary column (30 m, i.d. 0.25 mm, film 0.25 µm) and an Agilent 5975C mass spectrometer. The volatiles were analyzed by gas chromatography (GC) using a two step temperature gradient starting at 60° C. for 1 min, then going to 200° C. at 15° C./min, then to 260° C. at 25° C./min Headspace concentrations (in ng/L air) were obtained by external standard calibrations of the corresponding fragrance aldehydes and ketones in the single ion monitoring mode using ethanol solutions of five different concentrations. 0.2 µl of the different calibration solutions were injected onto Tenax® cartridges, which were immediately desorbed under the same conditions as those resulting from the headspace sampling.

The following headspace concentrations were measured on the different substrates in the absence (reference) or in the presence of one of the diamines C, F, G and N. All data are average values of at least two measurements, values were rounded. The results are reported in the following tables.

TABLE 5

Results obtained by evaporation from an APC film spread onto glass plates

| | Headspace concentrations for a mixture of aldehydes and ketones [ng/L] (1 day after deposition) | | | | |
|---|---|---|---|---|---|
| | Reference | C | F | G | N |
| Furfural | 0.4 | 11.3 | 1.3 | 0.9 | 0.4 |
| 2-Heptanone | 0.1 | 0.1 | 0.1 | 0.1 | 0.1 |
| Benzaldehyde | 1.5 | 1.9 | 2.0 | 1.2 | 1.3 |
| 3,5,5-Trimethylhexanal | 0.2 | 1.5 | 2.3 | 0.3 | 0.5 |
| Triplal ® | 0.2 | 0.3 | 0.4 | 0.2 | 0.2 |
| 2,4,6-Trimethyl-3-cyclohexene-1-carbaldehyde | 0.0 | 0.1 | 0.1 | 0.0 | 0.0 |
| 4-Ethylbenzaldehyde | 0.2 | 1.0 | 2.2 | 1.1 | 0.7 |
| 4-Methylacetophenone | 1.2 | 0.2 | 0.7 | 0.6 | 0.4 |
| Trifernal ® | 5.0 | 10.0 | 12.1 | 5.7 | 9.8 |
| Decanal | 4.6 | 5.5 | 7.0 | 3.5 | 6.2 |
| Methoxymelonal | 13.3 | 9.7 | 15.5 | 10.2 | 15.0 |
| Benzylacetone | 0.3 | 0.4 | 0.5 | 0.5 | 0.1 |
| Delphone | 9.8 | 1.9 | 6.8 | 4.4 | 4.6 |
| 1,8-p-Menthadien-7-al | 0.3 | 2.2 | 4.7 | 1.4 | 1.4 |
| 2-Methyldecanal | 1.3 | 1.0 | 2.9 | 1.6 | 1.6 |
| 10-Undecenal | 3.0 | 4.8 | 6.8 | 3.0 | 5.2 |
| Liminal ® | 0.5 | 4.3 | 7.1 | 2.2 | 4.0 |

TABLE 5-continued

Results obtained by evaporation from an APC film spread onto glass plates

| | Headspace concentrations for a mixture of aldehydes and ketones [ng/L] (1 day after deposition) | | | | |
|---|---|---|---|---|---|
| | Reference | C | F | G | N |
| Vertral ® | 1.5 | 3.4 | 6.0 | 2.1 | 2.7 |
| $\Delta I_{mix}$ | 1 | 7.4 | 4.6 | 1.7 | 1.8 |

C = (cis/trans)-N,N'-bis(2-furanylmethyl)cyclohexane-1,2-diamine;
F = (cis/trans)-N,N'-bis((5-methylfuran-2-yl)methyl)cyclohexane-1,2-diamine;
G = (cis/trans)-(5,5'-((cyclohexane-1,2-diylbis(azanediyl))bis(methylene))bis(furan-5,2-diyl))dimethanol;
N = N-((1H-pyrrol-2-yl)methyl)-1-(piperidin-2-yl)methanamine.

TABLE 6

Results obtained by evaporation from an APC film spread onto porous ceramic plates

| | Headspace concentrations for a mixture of aldehydes and ketones [ng/L] (1 day after deposition) | | | | |
|---|---|---|---|---|---|
| | Reference | C | F | G | N |
| Furfural | 0.5 | 13.3 | 2.4 | 2.1 | 0.6 |
| 2-Heptanone | 0.1 | 0.1 | 0.1 | 0.1 | 0.1 |
| Benzaldehyde | 1.9 | 1.9 | 2.5 | 1.8 | 1.5 |
| 3,5,5-Trimethylhexanal | 0.4 | 1.5 | 3.0 | 0.4 | 0.6 |
| Triplal ® | 0.4 | 0.2 | 0.8 | 0.3 | 0.3 |
| 2,4,6-Trimethyl-3-cyclohexene-1-carbaldehyde | 0.1 | 0.1 | 0.2 | 0.1 | 0.1 |
| 4-Ethylbenzaldehyde | 0.5 | 1.2 | 2.8 | 1.5 | 0.7 |
| 4-Methylacetophenone | 1.8 | 0.6 | 1.4 | 0.9 | 1.0 |
| Trifernal ® | 9.4 | 21.9 | 30.3 | 17.1 | 18.3 |
| Decanal | 6.9 | 17.4 | 24.3 | 19.1 | 12.5 |
| Methoxymelonal | 6.6 | 7.0 | 13.7 | 7.8 | 6.6 |
| Benzylacetone | 1.2 | 0.7 | 1.1 | 0.8 | 0.5 |
| Delphone | 8.6 | 2.9 | 7.1 | 4.7 | 5.8 |
| 1,8-p-Menthadien-7-al | 1.1 | 2.7 | 7.5 | 1.9 | 1.5 |
| 2-Methyldecanal | 2.3 | 1.4 | 3.5 | 1.9 | 1.9 |
| 10-Undecenal | 7.4 | 17.7 | 24.9 | 19.1 | 14.7 |
| Liminal ® | 1.2 | 14.7 | 27.0 | 14.2 | 9.2 |
| Vertral ® | 3.4 | 5.0 | 13.7 | 4.7 | 3.8 |
| $\Delta I_{mix}$ | 1 | 6.8 | 4.9 | 2.6 | 1.6 |

C = (cis/trans)-N,N'-bis(2-furanylmethyl)cyclohexane-1,2-diamine;
F = (cis/trans)-N,N'-bis((5-methylfuran-2-yl)methyl)cyclohexane-1,2-diamine;
G = (cis/trans)-(5,5'-((cyclohexane-1,2-diylbis(azanediyl))bis(methylene))bis(furan-5,2-diyl))dimethanol;
N = N-((1H-pyrrol-2-yl)methyl)-1-(piperidin-2-yl)methanamine.

The data show that the presence of a diamine derivative according to the present invention increases the headspace concentrations of most volatile compounds from the mixture with respect to the reference without diamine. The structure of the diamine derivative, the nature of the substituent at the N-atom of the diamine, and the type of surface influence the performance of the dynamic mixture. Therefore, the use of diamine derivatives according to the present invention improves the overall performance of volatile compounds in APCs from different types of surfaces by the in situ formation of dynamic mixtures.

What is claimed is:

1. A method to confer, enhance, improve or modify the odor properties of a perfuming composition or of a perfumed article, which method comprises adding to said composition or article an effective amount of a dynamic mixture, for the controlled release of perfuming aldehydes or ketones, obtainable by reacting, in a water-containing medium, i) at least two perfuming aldehydes and/or ketones each having a molecular weight comprised between 80 and 230 g/mol; with ii) at least one derivative of formula

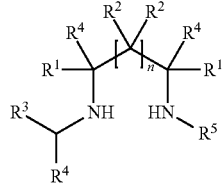

(I)

wherein: n is 0 or 1;

each $R^1$ represents, independently of each other, a hydrogen atom, a phenyl group optionally substituted, or a $C_{1-10}$ alkyl or alkenyl group optionally substituted; if n =0, two $R^1$ taken together represent a $C_4$ group forming with the carbon atoms to which they are linked an aromatic ring which is optionally substituted;

each $R^2$ represents, independently of each other, a hydrogen atom, a phenyl group optionally substituted, or a $C_{1-10}$ alkyl or alkenyl group optionally substituted; two $R^2$ or two $R^1$ or one $R^1$ and one $R^2$, taken together, may form a $C_{3-8}$ alkanediyl or alkenediyl group;

$R^3$ represents a $C_{3-5}$ heteroaryl group optionally substituted; or $R^3$ and the adjacent $R^1$, taken together, represent with the carbon atoms to which they are linked and the NH group between them a 1 H-pyrrole ring;

each $R^4$ represents, independently of each other, a hydrogen atom or a methyl group; and $R^5$ represents a $CHR^3R^4$ group, a benzyl group optionally substituted or a $C_{1-10}$ alkyl or alkenyl group; or $R^5$ and the adjacent R1, taken together, represent a $C_{3-5}$ group forming with the carbon and nitrogen atom to which they are linked a saturated ring which is optionally substituted with a $CHR^3R^4$ group or a $CH_2NHCHR^3R^4$ group or one or two $C_{1-4}$ alkyl groups;

and wherein the substituents of said $R^1$ or $R^2$ are one, two or three groups of $NR^6{}_2$, $(NR^6R^7{}_2)X$, $OR^7$, $SO_3M$, $COOR^8$ or $R^6$, with $R^6$ representing a phenyl group optionally substituted by a $C_1$-$C_{10}$, or $C_1$-$C_4$, hydrocarbon group or representing a $C_1$ to $C_{10}$ alkyl or alkenyl group optionally comprising from 1 to 5 oxygen atoms, $R^7$ representing a hydrogen atom or a $R^6$ group, M representing a hydrogen atom or an alkali metal ion, $R^8$ representing a M group or a $R^6$ group and X representing a halogen atom or a sulphate; and wherein the substituents of said $R^3$ or $R^5$ are one, two or three groups selected amongst i) halogens, ii) $C_{5-12}$ cycloalkyl or cycloalkenyl, iii) $C_{1-10}$ alkoxy, alkyl, alkenyl, polyalkyleneglycols or halo- or perhalo-hydrocarbons, iv) $COOR^8$ wherein $R^8$ is as defined above, v) $CH_2OH$ or CHO groups, or vi) a benzyl group or a fused or non-fused phenyl or indanyl group, said groups being optionally substituted by one, two or three halogen, $C_{1-8}$ alkyl, alkoxy, amino, nitro, ester, sulfonate or halo- or perhalo- hydrocarbon groups.

2. A method according to claim 1, wherein the derivative of formula (I) is a compound of formula

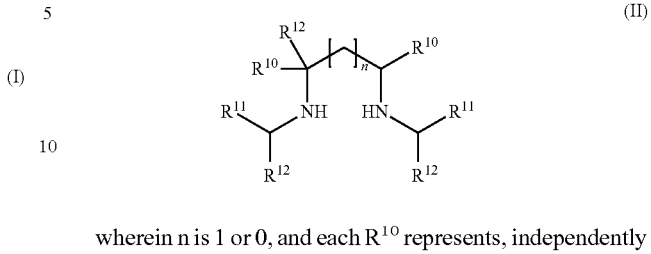

(II)

wherein n is 1 or 0, and each $R^{10}$ represents, independently of each other, a hydrogen atom, a phenyl group optionally substituted, or a $C_{1-4}$ alkyl group; when n is 0 the two $R^{10}$, taken together, may form a linear or branched $C_{3-6}$ alkanediyl group;

each $R^{11}$ represents, independently of each other, a $C_{3-5}$ heteroaryl group optionally substituted or one is a $C_{3-5}$ heteroaryl group optionally substituted and the other is a phenyl group optionally substituted; or one $R^{11}$ and one adjacent $R^{10}$ are taken together and represent a $C_{3-5}$ group forming with the carbon atoms to which they are linked and the NH group between them a saturated or a 1 H-pyrrole ring which is optionally substituted; and each $R^{12}$ represents, independently of each other, a hydrogen atom or a methyl group; the substituents of said $R^{10}$ are one, two or three groups of $OR^{7'}$, $SO_3M$, $COOR^{8'}$ or $R^{6'}$, with $R^{6'}$ representing a $C_{1-4}$ alkyl group optionally comprising from 1 to 2 oxygen atoms, $R^{7'}$ representing a hydrogen atom or a $R^{6'}$ group, M representing a hydrogen atom or an alkali metal ion, $R^{8'}$ representing a M group or a $R^{6'}$ group;

wherein the substituents of said $R^{11}$ are one or two selected amongst ii) $C_{5-6}$ cycloalkyl groups, iii) $C_{1-6}$ alkoxy or alkyl groups, iv) $COOR^8$ wherein $R^8$ is as defined above, v) $CH_2OH$ or CHO groups, or vi) a benzyl group or a fused or non-fused phenyl or indanyl group, said group being optionally substituted by one or two halogen, $C_{1-6}$ alkyl, alkoxy, amino, ester, sulfonate or perhalo-hydrocarbon groups.

3. The method according to claim 2, wherein said $R^4$ or $R^{12}$ represents each a hydrogen atom.

4. The method according to claim 2, wherein said $R^1$ or $R^{10}$ represents each a hydrogen atom or a phenyl group optionally substituted, or a methyl group; or the two $R^1$, or the two $R^{10}$, when taken together, form a linear $C_{3-4}$ alkanediyl group.

5. The method according to claim 2, wherein said $R^3$ or $R^{11}$ represents each a $C_{3-5}$ 2-heteroaryl group which is optionally substituted.

6. The method according to claim 2, wherein said derivative of formula (I) or (II) is a compound of any of the formulae (III) to (VI)

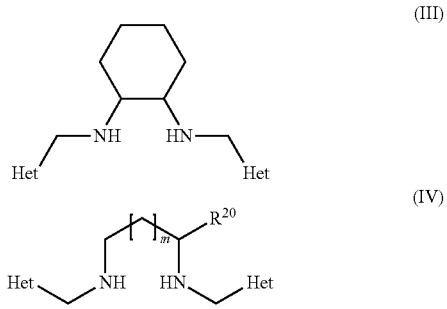

(III)

(IV)

-continued

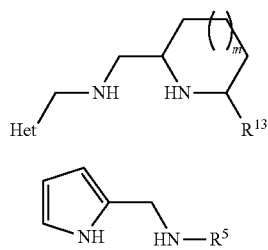
(V)

(VI)

wherein m is 0 or 1, $R^5$ is a $CHR^3R^4$ group, a benzyl group optionally substituted, or a $C_{1-10}$ alkyl or alkenyl group Het is a $C_{3-5}$ heteroaryl group optionally substituted, $R^{20}$ represents a hydrogen atom or a $C_{1-3}$ alkyl group, and $R^{13}$ represents a hydrogen atom or a $CH_2$Het or $CH_2NHCH_2$Het group or a Alk group, Alk being a $C_{1-3}$ alkyl group optionally comprising a OH or COOM group, M being an alkali metal cation.

7. The method according to claim 1, wherein said perfuming aldehydes and/or ketones are characterized by a vapor pressure comprised between above 7.0 Pa and below 450 Pa.

8. The method according to claim 1, wherein said dynamic mixture is obtained by reacting together at least one derivative of formula (I) with at least five perfuming aldehydes and/or ketones.

9. A dynamic mixture, for the controlled release of perfuming aldehydes or ketones, obtainable by reacting, in a water-containing medium
   i) at least two perfuming aldehydes and/or ketones each having a molecular weight comprised between 80 and 230 g/mol; with
   ii) at least one derivative of formula

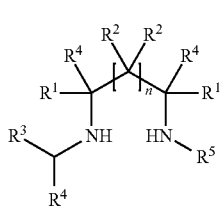
(I)

wherein:
n is 0 or 1;
each $R^1$ represents, independently of each other, a hydrogen atom, a phenyl group optionally substituted, or a $C_{1-10}$ alkyl or alkenyl group optionally substituted; if n =0, two $R^1$ taken together represent a $C_4$ group forming with the carbon atoms to which they are linked an aromatic ring which is optionally substituted;
each $R^2$ represents, independently of each other, a hydrogen atom, a phenyl group optionally substituted, or a $C_{1-10}$ alkyl or alkenyl group optionally substituted; two $R^2$ or two $R^1$ or one $R^1$ and one $R^2$, taken together, may form a $C_{3-8}$ alkanediyl or alkenediyl group;
$R^3$ represents a $C_{3-5}$ heteroaryl group optionally substituted; or $R^3$ and the adjacent $R^1$, taken together, represent with the carbon atoms to which they are linked and the NH group between them a 1 H-pyrrole ring;
each $R^4$ represents, independently of each other, a hydrogen atom or a methyl group; and
$R^5$ represents a $CHR^3R^4$ group, a benzyl group optionally substituted or a $C_{1-10}$ alkyl or alkenyl group; or $R^5$ and the adjacent $R^1$, taken together, represent a $C_{3-5}$ group forming with the carbon and nitrogen atom to which they are linked a saturated ring which is optionally substituted with a $CHR^3R^4$ group or a $CH_2NHCHR^3R^4$ group or one or two $C_{1-4}$ alkyl groups;
and wherein the substituents of said $R^1$ or $R^2$ are one, two or three groups of $NR^6_2$, $(NR^6R^7_2)X$, $OR^7$, $SO_3M$, $COOR^8$ or $R^6$, with $R^6$ representing a phenyl group optionally substituted by a $C_1$-$C_{10}$, or $C_1$-$C_4$, hydrocarbon group or representing a $C_1$ to $C_{10}$ alkyl or alkenyl group optionally comprising from 1 to 5 oxygen atoms, $R^7$ representing a hydrogen atom or a $R^6$ group, M representing a hydrogen atom or an alkali metal ion, $R^8$ representing a M group or a $R^6$ group and X representing a halogen atom or a sulphate; and
the substituents of said $R^3$ or $R^5$ are one, two or three groups selected amongst i) halogens. ii) $C_{5-12}$ cycloalkyl or cycloalkenyl, iii) $C_{1-10}$ alkoxy, alkyl, alkenyl, polyalkyleneglycols or halo- or perhalo-hydrocarbons, iv) $COOR^8$ wherein $R^8$ is as defined above, v) $CH_2OH$ or CHO groups, or vi) a benzyl group or a fused or non-fused phenyl or indanyl group, said groups being optionally substituted by one, two or three halogen, $C_{1-8}$ alkyl, alkoxy, amino, nitro, ester, sulfonate or halo- or perhalo-hydrocarbon groups.

10. A method to confer, enhance, improve or modify the odor properties of a perfuming composition or of a perfumed article, which method comprises adding to said composition or article an amount of the dynamic mixture of claim 9 effective to provide controlled release of the perfuming aldehydes or ketones therefrom.

11. A method to confer, enhance, improve or modify the odor properties of a perfuming composition or of a perfumed article, which method comprises adding to said composition or article an effective amount of a dynamic mixture, for the controlled release of perfuming aldehydes or ketones, obtained by reacting, in a water-containing medium,
   i) at least two perfuming aldehydes and/or ketones each having a molecular weight comprised between 80 and 230 g/mol; with
   ii) at least one derivative of formula

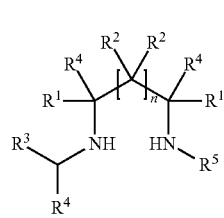
(I)

wherein: n is 0 or 1;
each $R^1$ represents, independently of each other, a hydrogen atom, a phenyl group optionally substituted, or a $C_{1-10}$ alkyl or alkenyl group optionally substituted; if n =0, two $R^1$ taken together represent a $C_4$ group forming with the carbon atoms to which they are linked an aromatic ring which is optionally substituted;
each $R^2$ represents, independently of each other, a hydrogen atom, a phenyl group optionally substituted, or a $C_{1-10}$ alkyl or alkenyl group optionally substituted; two $R^2$ or two $R^1$ or one $R^1$ and one $R^2$, taken together, may form a $C_{3-8}$ alkanediyl or alkenediyl group;
$R^3$ represents a $C_{3-5}$ heteroaryl group optionally substituted; or $R^3$ and the adjacent $R^1$, taken together, represent with the carbon atoms to which they are linked and the NH group between them a 1 H-pyrrole ring;
each $R^4$ represents, independently of each other, a hydrogen atom or a methyl group; and $R^5$ represents a $CHR^3R^4$ group, a benzyl group optionally substituted or a $C_{1-10}$ alkyl or alkenyl group; or $R^5$ and the adjacent R1, taken together, represent a $C_{3-5}$ group forming with the carbon and nitrogen atom to which they are linked a saturated ring which is optionally substituted with a $CHR^3R^4$ group or a $CH_2NHCHR^3R^4$ group or one or two $C_{1-4}$ alkyl groups;

and wherein the substituents of said $R^1$ or $R^2$ are one, two or three groups of $NR^6_2$, $(NR^6R^7_2)X$, $OR^7$, $SO_3M$, $COOR^8$ or $R^6$, with $R^6$ representing a phenyl group optionally substituted by a $C_1$-$C_{10}$, or $C_1$-$C_4$, hydrocarbon group or representing a $C_1$ to $C_{10}$ alkyl or alkenyl group optionally comprising from 1 to 5 oxygen atoms, $R^7$ representing a hydrogen atom or a $R^6$ group, M representing a hydrogen atom or an alkali metal ion, $R^8$ representing a M group or a $R^6$ group and X representing a halogen atom or a sulphate; and the substituents of said $R^3$ or $R^5$ are one, two or three groups selected amongst i) halogens, ii) $C_{5-12}$ cycloalkyl or cycloalkenyl, iii) $C_{1-10}$ alkoxy, alkyl, alkenyl, polyalkyleneglycols or halo- or perhalo-hydrocarbons, iv) $COOR^8$ wherein $R^8$ is as defined above, v) $CH_2OH$ or CHO groups, or vi) a benzyl group or a fused or non-fused phenyl or indanyl group, said groups being optionally substituted by one, two or three halogen, $C_{1-8}$ alkyl, alkoxy, amino, nitro, ester, sulfonate or halo- or perhalo-hydrocarbon groups.

12. A method according to claim 1, wherein the perfuming aldehydes and/or ketones are selected from the group consisting of the $C_{5-20}$ perfuming aldehydes and/or the $C_{5-20}$ perfuming ketones.

13. A method according to claim 4, wherein the two $R^1$ or the two $R^{10}$, when taken together, form a linear $(CH_2)_4$ group.

14. The dynamic mixture according to claim 9, wherein the perfuming aldehydes and/or ketones are selected from the group consisting of the $C_{5-20}$ perfuming aldehydes and/or the $C_{5-20}$ perfuming ketones.

15. A method according to claim 11, wherein the perfuming aldehydes and/or ketones are selected from the group consisting of the $C_{5-20}$ perfuming aldehydes and/or the $C_{5-20}$ perfuming ketones.

16. A method according to claim 11, wherein the derivative of formula (I) is a compound of formula

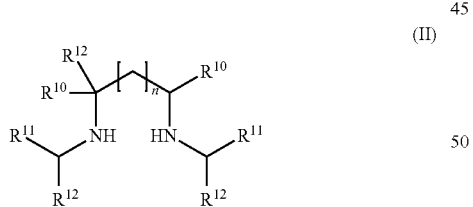

(II)

wherein n is 1 or 0, and each $R^{10}$ represents, independently of each other, a hydrogen atom, a phenyl group optionally substituted, or a $C_{1-4}$ alkyl group; when n is 0 the two $R^{10}$, taken together, may form a linear or branched $C_{3-6}$ alkanediyl group;

each $R^{11}$ represents, independently of each other, a $C_{3-5}$ heteroaryl group optionally substituted or one is a $C_{3-5}$ heteroaryl group optionally substituted and the other is a phenyl group optionally substituted; or one $R^{11}$ and one adjacent $R^{10}$ are taken together and represent a $C_{3-5}$ group forming with the carbon atoms to which they are linked and the NH group between them a saturated or a 1 H-pyrrole ring which is optionally substituted; and each $R^{12}$ represents, independently of each other, a hydrogen atom or a methyl group; the substituents of said $R^{10}$ are one, two or three groups of $OR^{7'}$, $SO_3M$, $COOR^{8'}$ or $R^{6'}$, with $R^{6'}$ representing a $C_{1-4}$ alkyl group optionally comprising from 1 to 2 oxygen atoms, $R^{7'}$ representing a hydrogen atom or a $R^{6'}$ group, M representing a hydrogen atom or an alkali metal ion, $R^{8'}$ representing a M group or a $R^{6'}$ group;

wherein the substituents of said $R^{11}$ are one or two selected amongst ii) $C_{5-6}$ cycloalkyl groups, iii) $C_{1-6}$ alkoxy or alkyl groups, iv) $COOR^8$ wherein $R^8$ is as defined above, v) $CH_2OH$ or CHO groups, or vi) a benzyl group or a fused or non-fused phenyl or indanyl group, said group being optionally substituted by one or two halogen, $C_{1-6}$ alkyl, alkoxy, amino, ester, sulfonate or perhalo-hydrocarbon groups.

17. The method according to claim 16, wherein said $R^4$ or $R^{12}$ represents each a hydrogen atom.

18. The method according to claim 16, wherein said $R^1$ or $R^{10}$ represents each a hydrogen atom or a phenyl group optionally substituted, or a methyl group; or the two $R^1$, or the two $R^{10}$, when taken together, form a linear $C_{3-4}$ alkanediyl group.

19. The method according to claim 16, wherein said $R^3$ or $R^{11}$ represents each a $C_{3-5}$ 2-heteroaryl group which is optionally substituted.

20. The method according to claim 16, wherein said derivative of formula (I) or (II) is a compound of any of the formulae (III) to (VI)

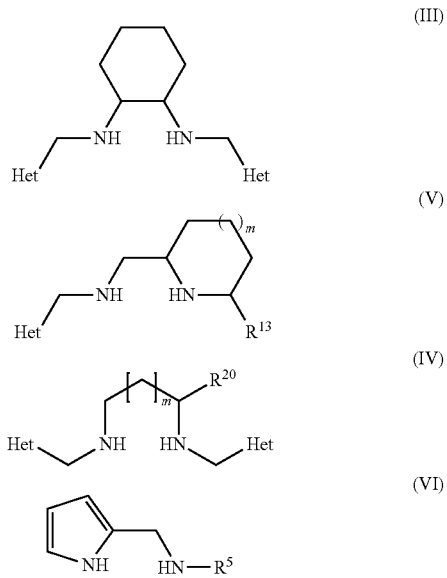

wherein m is 0 or 1, $R^5$ is a $CHR^3R^4$ group, a benzyl group optionally substituted, or a $C_{1-10}$ alkyl or alkenyl group Het is a $C_{3-5}$ heteroaryl group optionally substituted, $R^{20}$ represents a hydrogen atom or a $C_{1-3}$ alkyl group, and $R^{13}$ represents a hydrogen atom or a $CH_2Het$ or $CH_2NHCH_2Het$ group or a Alk group, Alk being a $C_{1-3}$ alkyl group optionally comprising a OH or COOM group, M being an alkali metal cation; and wherein said perfuming aldehydes and/or ketones are characterized by a vapor pressure comprised between above 7.0 Pa and below 450 Pa.

* * * * *

UNITED STATES PATENT AND TRADEMARK OFFICE
CERTIFICATE OF CORRECTION

PATENT NO. : 9,212,335 B2  
APPLICATION NO. : 14/111125  
DATED : December 15, 2015  
INVENTOR(S) : Herrmann et al.

Page 1 of 1

It is certified that error appears in the above-identified patent and that said Letters Patent is hereby corrected as shown below:

In the claims

Column 34:
Line 29, delete "$COOR^{8'}$ or $R^{6'}$, with $R^{6'}$" and insert -- $COOR^{8'}$ or $R^{6'}$, with $R^{6'}$ --;
Line 31, delete "$R^{6'}$" and insert -- $R^{6'}$ --;
Line 32, delete "$R^{8'}$" and insert -- $R^{8'}$ --;
Line 33, delete "$R^{6'}$" and insert -- $R^{6'}$ --.

Column 35:
Line 14, after "alkenyl", delete "group" and insert -- group, --.

Column 38:
Line 4, delete "$COOR^{8'}$ or $R^{6'}$, with $R^{6'}$" and insert -- $COOR^{8'}$ or $R^{6'}$, with $R^{6'}$ --;
Line 6, delete "$R^{6'}$" and insert -- $R^{6'}$ --;
Line 7, delete "$R^{8'}$" and insert -- $R^{8'}$ --;
Line 8, delete "$R^{6'}$" and insert -- $R^{6'}$ --;
Line 56, after "alkenyl", delete "group" and insert -- group, --.

Signed and Sealed this  
Twenty-third Day of February, 2016

Michelle K. Lee  
*Director of the United States Patent and Trademark Office*